US006989402B1

(12) United States Patent
Hangeland et al.

(10) Patent No.: US 6,989,402 B1
(45) Date of Patent: Jan. 24, 2006

(54) THYROID RECEPTOR LIGANDS AND METHOD II

(75) Inventors: Jon Hangeland, Morrisville, PA (US); Minsheng Zhang, Warren, NJ (US); Yolanda Caringal, Lawrenceville, NJ (US); Denis Ryono, Princeton, NJ (US); Yi-Lin Li, Huddinge (SE); Johan Malm, Skogas (SE); Ye Liu, Tullinge (SE); Neeraj Garg, Tumba (SE); Chris Litten, Tumba (SE); Ana Maria Garcia Collazo, Stockholm (SE); Konrad Koehler, Huddinge (SE)

(73) Assignee: Karo Bio AB, Huddinge (SE)

( * ) Notice: Subject to any disclaimer, the term of this patent is extended or adjusted under 35 U.S.C. 154(b) by 0 days.

(21) Appl. No.: 09/868,889

(22) PCT Filed: Dec. 23, 1999

(86) PCT No.: PCT/IB99/02084

§ 371 (c)(1),
(2), (4) Date: Sep. 14, 2001

(87) PCT Pub. No.: WO00/39077

PCT Pub. Date: Jul. 6, 2000

(30) Foreign Application Priority Data

Dec. 24, 1998 (GB) .................................. 9828442

(51) Int. Cl.
A61K 31/44 (2006.01)
A61K 31/192 (2006.01)
A61K 31/40 (2006.01)
A61K 31/4174 (2006.01)
C07D 211/56 (2006.01)
C07D 213/72 (2006.01)
C07D 229/38 (2006.01)
C07D 265/30 (2006.01)
C07D 241/04 (2006.01)
C07D 207/14 (2006.01)

(52) U.S. Cl. .................... 514/563; 514/237.8; 514/398; 514/399; 514/563; 544/162; 544/402; 546/224; 546/309; 548/371.4; 548/567; 562/444; 562/449

(58) Field of Classification Search ................ 514/538, 514/539, 563, 237.8, 398, 399; 562/444, 562/449, 450; 546/309, 224; 548/567, 371.4; 544/162, 402
See application file for complete search history.

(56) References Cited

U.S. PATENT DOCUMENTS 4,741,897 A 5/1988 Andrews et al.
6,395,784 B1 * 5/2002 Ryono ........................ 514/563

FOREIGN PATENT DOCUMENTS

DE 32 31 541 A 3/1994
EP 0 580 550 1/1994
WO WO 96/40048 A 2/1996

OTHER PUBLICATIONS

M. Adamczyk, et al: Bioconjugate Chem., vol. 8, No. 2, pp. 133-145, XP000906993 (1997).
M. Andre, et al: J. Chromatogr. A, vol. 725, No. 2, pp. 287-294, XP004039616 (1996).
Database Chemabs [Online} Chemical Abstracts Service, Columbus, Ohio, US STN, Caplus accession No. 1971: 540431, XP002139408—& Chemical Abstracts, vol. 75, No. 23, Dec. 6, 1971 Columbus, Ohio US; abstract No. 140431, XP002139407 & K. Masuda et al: Takeda Kenkyusho Ho, vol. 29, No. 4, pp. 545-552 (1970).

* cited by examiner

Primary Examiner—Joseph K. McKane
Assistant Examiner—Janet L. Coppins
(74) Attorney, Agent, or Firm—Todd E. Garabedian; Wiggin and Dana LLP

(57) ABSTRACT

New thyroid receptor ligands are provided which have general formula (I) in which: n is an integer from 0 to 4; $R_1$ is halogen, trifluoromethyl, or alkyl of 1 to 6 carbons or cycloalkyl of 3 to 7 carbons; $R_2$ and $R_3$ are the same or different and are hydrogen, halogen, alkyl of 1 to 4 carbons or cycloalkyl of 3 to 5 carbons, at least one of $R_2$ and $R_3$ being other than hydrogen; $R_4$ is a carboxylic acid amide (CONR'R") or an acylsulphonamide (CONHSO2R') derivative, or a pharmaceutically acceptable salt thereof, and all stereoisomers thereof; or when n is equal to or greater than one, $R_4$ may be a heteroaromatic moiety which may be substituted or unsubstituted, or an amine (NR'R"). $R_5$ is hydrogen or an acyl (such as acetyl or benzoyl) or other group capable of bioconversion to generate the free phenol structure (wherein $R_5$=H). In addition, a method is provided for preventing, inhibiting or treating a disease associated with metabolism dysfunction or which is dependent upon the expression of a $T_3$ regulated gene, wherein a compound as described above is administered in a therapeutically effective amount. Examples of such diseases associated with metabolism dysfunction or are dependent upon the expression of a $T_3$ regulated gene include obesity, hypercholesterolemia, atherosclerosis, cardiac arrhythmias, depression, osteoporosis, hypothyroidism, goiter, thyroid cancer as well as glaucoma, congestive heart failure and skin disorders.

21 Claims, No Drawings

THYROID RECEPTOR LIGANDS AND METHOD II

FIELD OF THE INVENTION

This invention relates to novel compounds which are thyroid receptor ligands, and are preferably selective for the thyroid hormone receptor β, to methods of preparing such compounds and to methods for using such compounds such as in the regulation of metabolism.

BACKGROUND OF THE INVENTION

While the extensive role of thyroid hormones in regulating metabolism in humans is well recognized, the discovery and development of new specific drugs for improving the treatment of hyperthyroidism and hypothyroidism has been slow. This has also limited the development of thyroid hormone agonists and antagonists for treatment of other important clinical indications, such as hypercholesterolemia, obesity and cardiac arrhythmias.

Thyroid hormones affect the metabolism of virtually every cell of the body. At normal levels, these hormones maintain body weight, the metabolic rate, body temperature, and mood, and influence serum low density lipoprotein (LDL) levels, Thus, in hypothyroidism there is weight gain, high levels of LDL cholesterol, and depression. In excess with hyperthyroidism, these hormones lead to weight loss, hypermetabolism, lowering of serum LDL levels, cardiac arrhythmias, heart failure, muscle weakness, bone loss in postmenopausal women, and anxiety.

Thyroid hormones are currently used primarily as replacement therapy for patients with hypothyroidism. Therapy with L-thyroxine returns metabolic functions to normal and can easily be monitored with routine serum measurements of levels of thyroid-stimulating hormone (TSH), thyroxine (3,5,3',5'-tetraiodo-L-thyronine, or $T_4$) and triiodothyronine (3,5,3'-triiodo-L-thyronine, or $T_3$). However, replacement therapy, particularly in older individuals is limited by certain of the deleterious effects of thyroid hormones.

In addition, some effects of thyroid hormones may be therapeutically useful in non-thyroid disorders if adverse effects can be minimized or eliminated. These potentially useful influences include weight reduction, lowering of serum LDL levels, amelioration of depression and stimulation of bone formation. Prior attempts to utilize thyroid hormones pharmacologically to treat these disorders have been limited by manifestations of hyperthyroidism, and in particular by cardiovascular toxicity.

Development of specific and selective thyroid hormone receptor agonists could lead to specific therapies for these common disorders while avoiding the cardiovascular and other toxicities of native thyroid hormones. Tissue-selective thyroid hormone agonists may be obtained by selective tissue uptake or extrusion, topical or local delivery, targeting to cells through other ligands attached to the agonist and targeting receptor subtypes. Thyroid hormone receptor agonists that interact selectively with the β-form of the thyroid hormone receptor offers an especially attractive method for avoiding cardio-toxicity.

Thyroid hormone receptors (TRs) are, like other nuclear receptors, single polypeptide chains. The various receptor forms appear to be products of two different genes α and β. Further isoform differences are due to the fact that differential RNA processing results in at least two isoforms from each gene. The $TR\alpha_1$, $TR\beta_2$ and $TR\beta_2$ isoforms bind thyroid hormone and act as ligand-regulated transcription factors. In adults, the $TR\beta_1$ isoform is the most prevalent form in most tissues, especially in the liver and muscle. The $TR\alpha_2$ isoform is prevalent in the pituitary and other parts of the central nervous system, does not bind thyroid hormones, and acts in many contexts as a transcriptional repressor. The $TR\alpha_1$ isoform is also widely distributed, although its levels are generally lower than those of the $TR\beta_1$ isoform. This isoform may be especially important for development. Whereas many mutations in the TRβ gene have been found and lead to the syndrome of generalized resistance to thyroid hormone, mutations leading to impaired TRα function have not been found.

A growing body of data suggest that many or most effects of thyroid hormones on the heart, and in particular on the heart rate and rhythm, are mediated through the α-form of the TRα1 isoform, whereas most actions of the hormone such as on the liver, muscle and other tissues are mediated more through the β-forms of the receptor. Thus, a TRβ-selective agonist might not elicit the cardiac rhythm and rate influences of the hormones but would elicit many other actions of the hormones. It is believed that the α-form of the receptor is the major drive to heart rate for the following reasons:

1) tachycardia is very common in the syndrome of generalized resistance to thyroid hormone in which there are defective TRβ-forms, and high circulating levels of $T_4$ and $T_3$;
2) there was a tachycardia in the only described patient with a double deletion of the TRβ gene (Takeda et al, J. Clin. Endrocrinol. & Metab. 1992, Vol. 74, p. 49);
3) a double knockout TRα gene (but not β-gene) in the mouse has a slower pulse than control mice; and,
4) western blot analysis of human myocardial TRs show presence of the $TR\alpha_1$, $TR\alpha_2$ and $TR\beta_2$ proteins, but not $TR\beta_1$.

If these indications are correct, then a TRβ-selective agonist could be used to mimic a number of thyroid hormone actions, while having a lesser effect on the heart. Such a compound may be used for: (1) replacement therapy in elderly subjects with hypothyroidism who are at risk for cardiovascular complications; (2) replacement therapy in elderly subjects with subclinical hypothyroidism who are at risk for cardiovascular complications; (3) obesity; (4) hypercholesterolemia due to elevations of plasma LDL levels; (5) depression; and, (6) osteoporosis in combination with a bone resorption inhibitor.

DESCRIPTION OF THE INVENTION

In accordance with the present invention, compounds are provided which are thyroid receptor ligands, and have the general formula I:

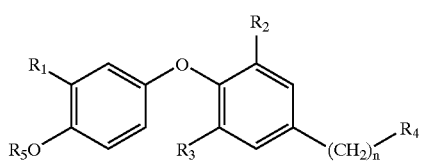

in which:
  n is an integer from 0 to 4;
  $R_1$ is halogen, trifluoromethyl, or alkyl of 1 to 6 carbons or cycloalkyl of 3 to 7 carbons;

$R_2$ and $R_3$ are the same or different and are hydrogen, halogen, alkyl of 1 to 4 carbons or cycloalkyl of 3 to 5 carbons, at least one of $R_2$ and $R_3$ being other than hydrogen;

$R_4$ is a heteroaromatic moiety which may be substituted or unsubstituted and is linked to $(CH_2)_n$ via a nitrogen atom or a carbon atom; an amine (NR'R"), including those in which the amine is derived from an alpha amino acid of either natural (L) or unnatural (D) stereochemistry; an acylsulphonamide ($CONHSO_2R'$) or a carboxylic acid amide (CONR'R") in which the amine portion of the carboxylic amide can be derived from an achiral or a L or D alpha amino acid such as when the general structure —CONR'R" can be represented by

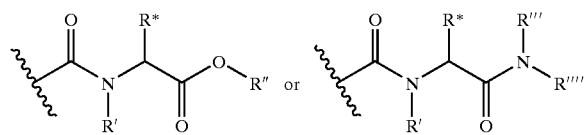

and R', R", R''' and R'''' are the same or different and are independently selected from hydrogen, alkyl, aryl and heteroaryl, substituted or unsubstituted, and R* may be hydrogen, alkyl, aryl and heteroaryl, substituted or unsubstituted, and may also be any of the side chains found in the naturally occuring alpha-amino acids and their analogs, including those examples wherein R' and R* are connected to form 4 to 8-membered rings (such as when R' and R* comprise consecutive —($CH_2$)— groups to form proline or homoproline); and with the proviso that when n equals zero (n=0), then $R_4$ can only be a carboxylic acid amide or an acylsulphonamide.

$R_5$ is hydrogen or an acyl (such as acetyl or benzoyl) or other group capable of bioconversion to generate the free phenol structure (wherein $R_5$=H);

including all stereoisomers thereof, prodrug esters thereof, and pharmaceutically acceptable salts thereof.

In addition, in accordance with the present invention, a method for preventing, inhibiting or treating a disease associated with metabolism dysfunction or which is dependent upon the expression of a $T_3$ regulated gene is provided, wherein a compound of formula I is administered in a therapeutically effective amount. The compound of formula I is preferably an agonist that is preferably selective for the thyroid hormone receptor-beta. Examples of such diseases associated with metabolism dysfunction or are dependent upon the expression of a $T_3$ regulated gene are set out hereinafter and include obesity, hypercholesterolemia, atherosclerosis, cardiac arrhythmias, depression, osteoporosis, hypothyroidism, goiter, thyroid cancer as well as glaucoma and congestive heart failure.

DETAILED DESCRIPTION OF THE INVENTION

The following definitions apply to the terms as used throughout this specification, unless otherwise limited in specific instances.

The term "thyroid receptor ligand" as used herein is intended to cover any moiety which binds to a thyroid receptor. The ligand may act as an agonist, an antagonist, a partial agonist or a partial antagonist.

The term "aliphatic hydrocarbon(s) as used herein refers to acyclic straight or branched chain groups which include alkyl, alkenyl or alkynyl groups.

The term "aromatic hydrocarbon(s) as used herein refers to groups including aryl groups as defined herein.

The term "heteroaryl" or "heteroaromatic moiety" as used herein alone or as a part of another group refers to a 5- or 6-membered aromatic ring which includes 1, 2, 3, or 4 heteroatoms, one of which must be a nitrogen atom; the other heteroatoms when present may be nitrogen, oxygen or sulfur, and such rings may be fused to another aryl or heteroaryl ring, and includes possible N-oxides. The heteroaryl group may optionally include 1 to 4 substituents such as aryl, alkyl, alkenyl, alkynyl, cycloalkyl, hydroxy, cyano, nitro, amino and/or carboxyl, and including the following

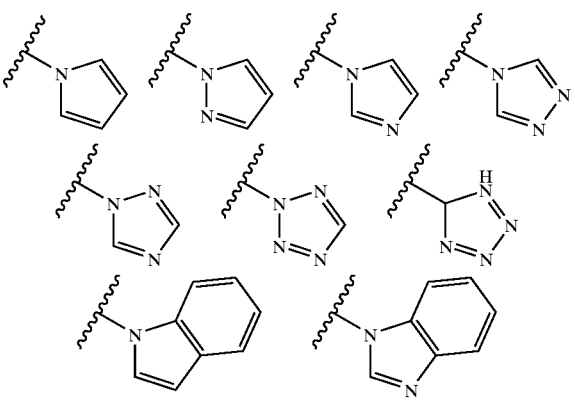

and the like.

Unless otherwise indicated, the term "lower alkyl", "alkyl" or "alk" as employed herein alone or as part of another group includes both straight and branched chain hydrocarbons, containing 1 to 12 carbons (in the case of alkyl or alk), in the normal chain, preferably 1 to 4 carbons, such as methyl, ethyl, propyl, isopropyl, butyl, t-butyl, or isobutyl, pentyl, hexyl, isohexyl, heptyl, 4,4-dimethylpentyl, octyl, 2,2,4-trimethylpentyl, nonyl, decyl, undecyl, dodecyl, which may be optionally substituted with 1 to 4 substituents which may include alkyl, alkenyl, alkynyl, aryl, cycloalkyl, heteroaryl, hydroxy, cyano, nitro, amino and/or carboxyl.

The term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may be optionally substituted through available carbon atoms with 1, 2, or 3 groups selected from hydrogen, halo, alkyl, haloalkyl, alkoxy, haloalkoxy, alkenyl, trifluoromethyl, trifluoromethoxy, alkynyl, hydroxy, amino, nitro, cyano and carboxylic acids.

Unless otherwise indicated, the term "lower alkenyl" or "alkenyl" as used herein by itself or as part of another group refers to straight or branched chain radicals of 2 to 12 carbons, preferably 2 to 5 carbons, in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, and the like, which may be substituted as in the case of "alkyl".

Unless otherwise indicated, the term "lower alkynyl" or "alkynyl" as used herein by itself or as part of another group refers to straight or branched chain radicals of 2 to 12 carbons, preferably 2 to 8 carbons, in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, which may be substituted as in the case of "alkyl".

Unless otherwise indicated, the term "cycloalkyl" as employed herein alone or as part of another group includes saturated cyclic hydrocarbon groups or partially unsaturated (containing 1 or 2 double bonds) cyclic hydrocarbon groups, containing one ring and a total of 3 to 7 carbons, preferably 3 to 5 carbons, forming the ring, which includes cyclopropyl, cyclobutyl, cyclopentyl, cyclohexyl, cycloheptyl, cyclopentenyl and cyclohexenyl, which may be substituted as in the case of "alkyl".

The term "halogen" or "halo" as used herein alone or as part of another group refers to chlorine, bromine, fluorine, and iodine as well as $CF_3$, with chlorine or bromine being preferred.

The compounds of formula I can be present as salts, in particular pharmaceutically acceptable salts. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$–$C_4$) alkyl or arylsulfonic acids which are unsubstituted or substituted, for example by halogen, for example methyl- or p-toluenesulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or trilower alkylamine, for example ethyl, tertbutyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

Preferred salts of the compounds of formula I which include a basic groups include monohydrochloride, hydrogensulfate, methanesulfonate, phosphate or nitrate.

Preferred salts of the compounds of formula I which include an acid group include sodium, potassium and magnesium salts and pharmaceutically acceptable organic amines.

Preferred are compounds of the invention of formula I wherein $R_1$ is isopropyl;

$R_2$ and $R_3$ are independently halogen such as bromo or chloro; or $R_2$ and $R_3$ are each methyl or one is methyl and the other is ethyl;

or one of $R_2$ and $R_3$ is halogen such as bromo or chloro, and the other is alkyl such as methyl, or hydrogen; and n is 0,1 or 2;

$R_4$ is carboxylic acid derivative of the type: amides, acylsulphonamides or an amide formed from an amino acid residue; and $R_5$ is hydrogen.

The most preferred compounds have the structures:

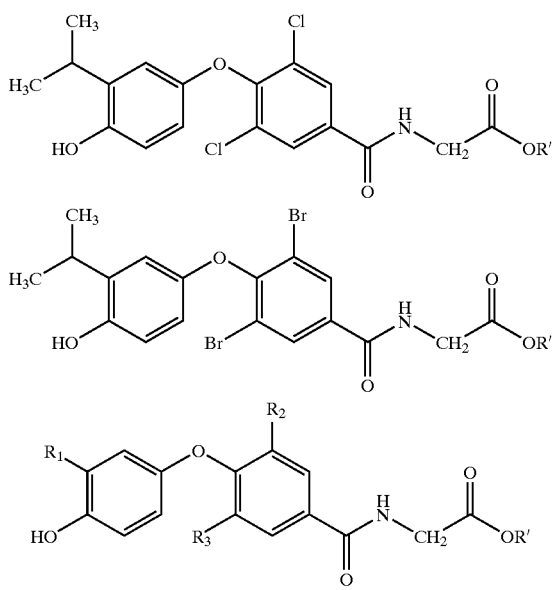

and other preferred compounds of the invention have the structures:

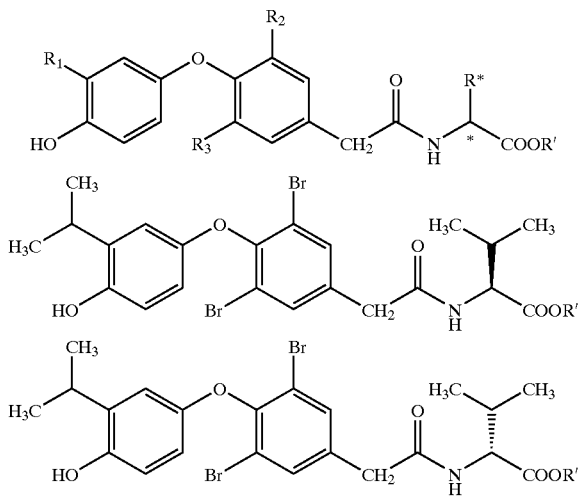

for or example
wherein $R_1$=isopropyl, methyl, ethyl, tertiary-butyl, cyclopentyl, cyclohexyl; $R_2$ and $R_3$ may be independently selected from Br, Cl and Me; R* may be hydrogen, alkyl, cycloalkyl, aryl and heteroaryl; * denotes either D or L stereochemistry; and R' and is selected from hydrogen, lower alkyl, especially ethyl and methyl or where the group COOR' represents prodrug ester forms known in the art such as pivaloyloxymethyl or dioxolenylmethyl. Such prodrug esters are described in standard references such as Chapter 31, written by Camille G. Wermuth et al., in "The Practice of Medicinal Chemistry", ed. C. G. Wermuth. Academic Press, 1996 (and the references contained therein).

The compounds of formula I may be prepared by the exemplary processes described in the following reaction schemes. Exemplary reagents and procedures for these reactions appear hereinafter and in the working Examples.

Compounds of formula I of the invention can be prepared using the sequence of steps outlined in Schemes 1 to 5 set out below.

Scheme 1 depicts a synthesis of compounds of formula I in which $R_4$=an amino acid, aniline derivative or aza containing heterocyclic ring, which through their nitrogen atom is connected to the aromatic ring by an intervening $(CH_2)_n$ group.

In Scheme 1, the amino acid, aniline derivative or aza containing heterocyclic ring, dissolved in a suitable solvent, is treated with 1–3 molar equivalents of an appropriate base, such as potassium carbonate, cesium carbonate, potassium hydroxide or sodium hydride. The resulting anion is then alkylated with the substituted iodide 5. Other combinations of alkylating agents or bases may be employed and are known to those skilled in the art. The reaction mixture is stirred at room temperature or heated until the starting materials are consumed. After standard work-up and purification, the methyl ether function is removed by treatment with 3–6 molar equivalents of a strong acid such as boron tribromide at 0° C. to 25° C. in an inert solvent such as dichloromethane. The reaction mixture gives after standard work-up and purification, the end products 6. Numerous alternative methodologies for the conversion of intermediates such as 3 and 4 to products 6 are well known to those skilled in the art.

Scheme 1 also outlines the preparation of the intermediate iodide 5, the sequence similar to what is employed in: "Novel Thyroid Receptor Ligands and Methods. Li. Yi-Lin; Liu, Ye; Hedfors, Asa; Malm, Johan; Mellin, Charlotta; Zhang, Minsheng. PCT Int. Appl., 40 pp. CODEN: PIXXD2. WO 9900353 A1 990107". An anisole-derived iodonium salt 2 and copper bronze in an inert solvent such as dichloromethane are mixed at room temperature. A mixture of the appropriate phenol ester 1 and a base such as triethylamine in an inert solvent such as dichloromethane was added to the mixture, generally using 2 molar equivalents each of the phenol and base, and 3 molar equivalents of iodonium salt 2. After stirring overnight at room temperature, the reaction mixture is purified via chromatography on silica gel, to give biaryl ether products 3. Other methods exist in the literature for the synthesis of diaryl ethers, for example, two references directly apply to the synthesis of thyroid hormone analogs: D. A. Evans et al., Tet. Letters, volume 39, 2937–2940 (1998) and G. M. Salamonczyk et al., Tet. Letters, volume 38, 6965–6968 (1997). The carboxylic acid ester can be hydrolyzed with a mixture of aqueous sodium hydroxide and methanol. The methyl ether function can be removed by treatment of the free acid product of the previous procedure with 4–6 molar equivalents of a strong acid such as boron tribromide at 0° C. in an inert solvent such as dichloromethane. Other combinations of protecting groups for the carboxylic acid present in 1 and phenolic hydroxyl in iodonium salt 2 can be employed, and their usage is known to those skilled in the art (references describing protecting group strategy include, for example, "Protecting Groups in Organic Chemistry", J. F. W. McOmie, Plenum Press, London, N.Y., 1973, and "Protective Groups in Organic Synthesis", T. W. Greene, Wiley, N.Y., 1984).

The intermediate ester product 3 is reduced by treatment with an appropriate reducing agent such as diisobutyl aluminium hydride in an inert solvent such as tetrahydrofuran at 0° C. If $R_2$ and $R_3$ are alkyl, then lithium aluminum hydride may be employed without the risk of reducing away halogen substituents at those positions. Standard work-up and purification yields the desired alcohol product 4. Other reducing agents may be employed and are known to those skilled in the art.

Intermediate 4 in Scheme 1 is finally converted to the intermediate iodide 5 by treatment of alcohol 4 with 2 molar quivalents of sodium iodide, phosphorous pentaoxide and phosphorous acid, and heated at 120° C. for 15 minutes. Numerous other methodologies for conversion of simple hydroxyl groups to the corresponding alkyl iodides are well known to those skilled in the art.

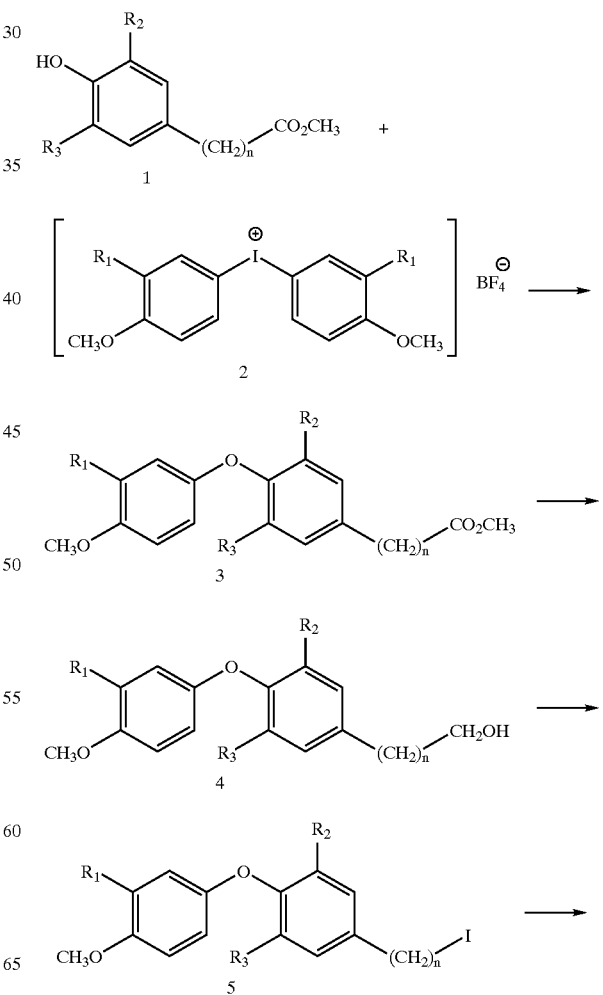

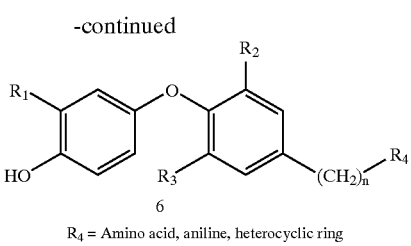

6

$R_4$ = Amino acid, aniline, heterocyclic ring

Scheme 2 depicts a synthesis of compounds of formula I in which $R_4$ is a tetrazole ring. Phenylacetonitrile 7 is readily prepared from benzylic iodide 5 by standard means such as reaction with sodium cyanide in a solvent mixture such as water/ethanol. Reaction of phenylacetonitrile 7, with sodium azide and ammonium chloride in dimethylformamide at elevated temperatures gives tetrazole derivatives 8 (Example 1 and 2), after standard work-up and purification procedures. In Example 2 this step was followed by a standard demethylation procedure, as above, in order to remove the protecting group.

Examples of substituted tetrazoles that can be prepared by further chemistry are also depicted in Scheme 2. Tetrazole derivative 8 can for instance be treated with an appropriate base such as sodium hydrogen carbonate in acetone, followed by N-alkylation with methyl iodide to afford derivatives 9 and 10, after standard work-up and purification procedures. Other alkylating agents and bases may be employed and are known to those skilled in the art.

3,5-dihalo-4-(4-hydroxy-3-isopropyl-phenoxy) carboxylic acids. The carboxylic acids 11 are readily obtained, for example, by hydrolysis of the corresponding esters 3.

In one procedure, a mixture of 11 with R=Me, a coupling reagent such as 3-ethyl-1-[3-(dimethylamino)propyl]carbodiimide hydrochloride (EDCI), and a base such as 1-hydroxybenzotriazole hydrate (HBT) in dichloromethane is stirred at room temperature. The appropriate protected amino acid and N-methylmorpholine is added. The reaction mixture yields after work-up and purification by either chromatography or recrystallization the corresponding coupled material, which after standard demethylation and hydrolysis procedures, gives the desired final amide products (Example 87).

Several examples of coupled products, employing different protecting groups for the carboxylic acid group was also prepared and isolated (Examples 29, 57, 71–72, 75, 77, 80–82, 84). Alternatively, amide end-products which contain free carboxylic acid groups can be re-esterified by standard procedures by, for instance, heating them in a mixture of refluxing methanol and thionyl chloride, to give the corresponding alkyl acid ester derivatives (Example 82).

In another more fruitful modification of the same procedure as above, 11 is kept unprotected (R=H) from the beginning of the sequence to give, after basic hydrolysis or treatment with a Lewis acid as $BBr_3$, and standard work-up and purification procedures, other examples of carboxylic acid amides (Example 3–24, 25–28, 56, 73–74, 76, 78–79, 83, 85–86, 203, 207–208).

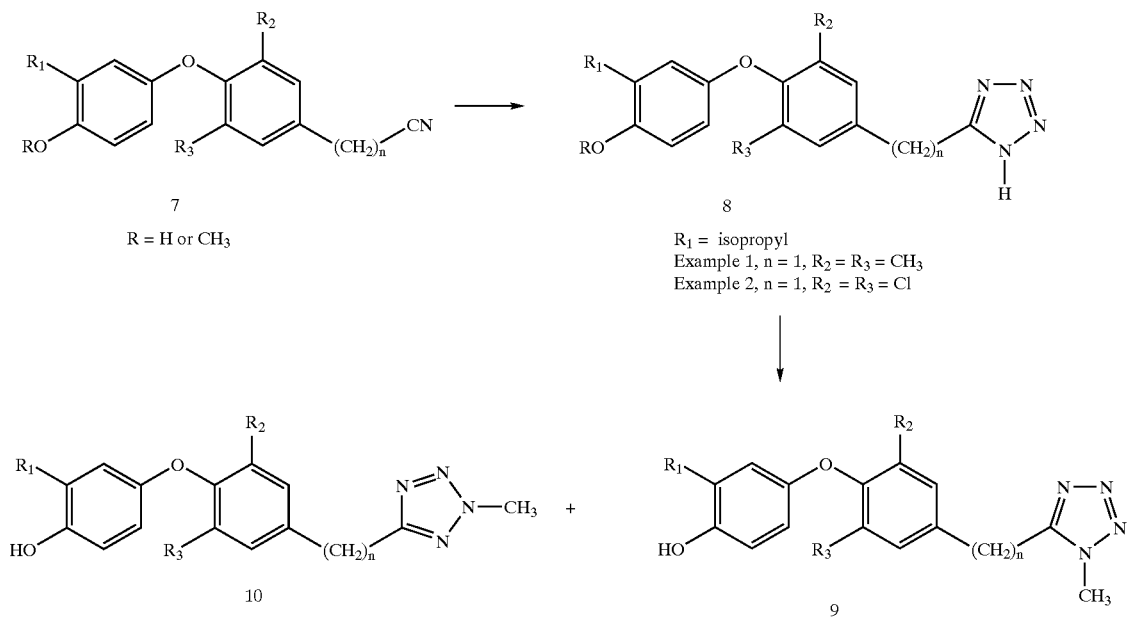

Scheme 2

Examples of compounds of formula I in which $R_4$ is an amide produced by coupling to an amino acid are shown in Scheme 3. The following procedures all involve the coupling of benzoic or acetic acid derivative 11 (n=0 or 1), with its phenolic hydroxyl group either protected by a methyl, left unprotected or bound to a resin, with various protected amino acids, to afford the corresponding amides 10 of An amide library can also be prepared by solid phase synthesis (Examples 30–55). In this procedure a methyl ester of intermediate 11 is loaded on a resin such as a Merrifield resin by standard procedures, well known to those skilled in the art. The resulting resin is then treated with sodium hydroxide in methanol to provide the resin-bond free carboxylic acid form of 11. Each resin pin is then filled with a solution of the corresponding aminoacid ester, PyBOP (benzotriazole-1-yl-oxy-tris-pyrrolidino phosphonium hexafluorophosphate), HBT, and N,N-diisopropylethylamine (Hunig's base, DIEA) and an inert solvent such as dichloromethane and is stirred at room temperature for days. Other combinations of base and coupling reagents can be employed here with successful results. After treatment of each of the individual pins with an appropriate base such as aqueous potassium hydroxide and washing of the resin, the amides are disassembled from the resin by treatment of a mixture of trifluoroacetic acid, dimethylsulfite and water.

Several other related methodologies exist for the coupling of amino acids with aromatic, as well as non-aromatic, carboxylic acids in solution or solid phase and are known to those skilled in the art.

The amino acid product 12 can reduced by treatment with an appropriate reagent such as sodium borohydride in an polar solvent such as ethanol at room temperature. If $R_2$ and $R_3$ are alkyl, then lithium aluminum hydride may be employed without the risk of reducing the halogen substituents at those positions. Standard work-up and purification yields the desired alcohol product. Other reducing agents may be employed and are known to those skilled in the art.

and subsequent mild acid treatment during work-up and purification by HPLC, the desired acylsulphonamides (Example 58–70).

In an exemplified procedure, a mixture of 13 with R=Me, a coupling reagent such as 3-ethyl-1-[3-(dimethylamino)propyl]carbodiimide hydrochloride (EDCI), and a base such as dimethylaminopyridine (DMAP) and the appropriate sulphonamide in dichloromethane is stirred at room temperature. The reaction mixture yields after work-up and purification by either chromatography or recrystallization the corresponding coupled material, which after standard demethylation procedures, yields yet other acylsulphonamides.

Other combinations of protecting groups and procedures can be employed. For example, applying similar chemistry as above, but with $R=Si(CH_3)_2t$-Bu, gives further examples of acylsulphonamides after removal of the protecting silyl group with ammonium fluoride (Examples 88–91).

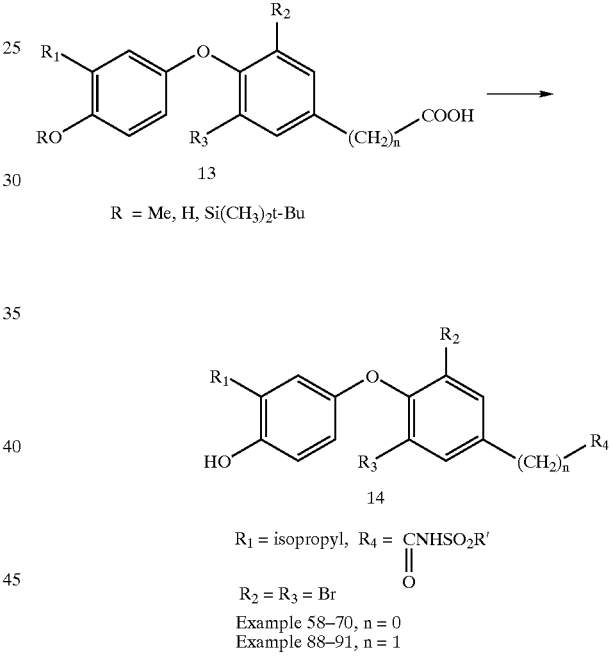

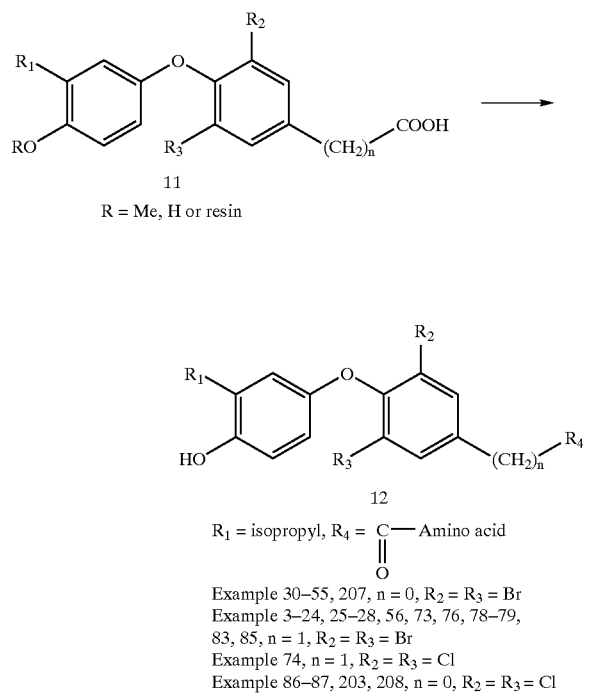

Scheme 4 depicts a synthesis of compounds of formula I in which $R_4$ is an acylsulphonamide. Similar procedures as for the coupling of amino acids above are employed.

In one procedure, 13 is kept unprotected (R=H), mixed with a base such as DIEA and the appropriate sulphonamide in dichloromethane. Dimethylformamide is added to the mixture if the sulphonamide does not dissolve completely. Treatment of the mixture with a base and coupling reagent combinations such as HOBt and PyBOP, gives after heating The procedures described in Scheme 5 further exemplify methods for the synthesis of compounds of formula I. Several structurally diverse amides, primary as well as secondary, were prepared as outlined in Scheme 5. Many alternative procedures for the coupling of amino acids above can be employed and are well known to those skilled in the art.

For example, in one procedure secondary diacetic acids amides are obtained through the treatment of 15 by dimethyliminodiacetate and EDCI in dimethylformamide or dichloromethane, followed by standard work-up procedures and final basic hydrolysis of the ester function (Example 206).

In another procedure, aromatic amides were obtained by a similar procedure as in Example 3–24 above (Example 192–202).

A library comprising 100 diverse primary and secondary amides was also prepared in an automated fashion, using standard literature methods (Example 92–191).

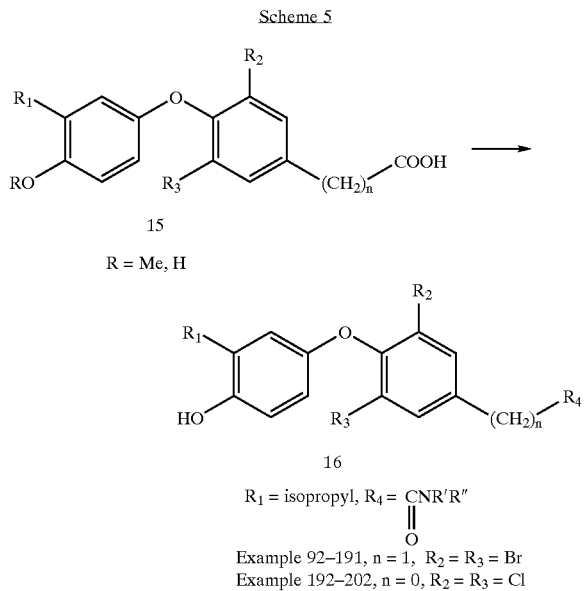

Scheme 5

15
R = Me, H

16
$R_1$ = isopropyl, $R_4$ = $CNR'R''$
                            ‖
                            O
Example 92–191, n = 1, $R_2$ = $R_3$ = Br
Example 192–202, n = 0, $R_2$ = $R_3$ = Cl With respect to the above reaction schemes, although the various $R_1$, $R_2$, $R_3$, $R_4$ and n moieties are specifically defined, unless otherwise indicated, it is to be understood that $R_1$, $R_2$, $R_3$, and $R_4$ may be any of the groups encompassed thereby and n may be 0, 1, 2, 3 or 4.

The compounds of the invention are agonist that are preferably selective for the thyroid hormone receptor-beta, and as such are useful in the treatment of obesity, hypercholesterolemia and atherosclerosis by lowering of serum LDL levels, alone or in combination with a lipid modulating drug such as an HMG-CoA reductase inhibitor, fibrate, thiazolidinedione, or MTP inhibitor, amelioration of depression alone or in combination with an antidepressant, and stimulation of bone formation to treat osteoporosis in combination with any known bone resorption inhibitor such as alendronate sodium. In addition, the compounds of the invention may be useful as replacement therapy in elderly patients with hypothyroidism or subclinical hypothyroidism who are at risk of cardiovascular complications, in the treatment of the elderly to provide a sense of well-being, and in the treatment of non-toxic goiter; in the management of papillary or follicular thyroid cancer (alone or with $T_4$); in the treatment of skin disorders such as psoriasis, glaucoma, cardiovascular disease such as in the prevention or treatment of atherosclerosis, and congestive heart failure.

The compounds of the invention may also be used to treat skin disorders or diseases involving dermal atrophy such as glucocorticoid induced dermal atrophy, including restoration of dermal atrophy induced by topical glucocorticoids, the prevention of dermal atrophy induced by topical glucocorticoids (such as the simultaneous treatment with topical glucocorticoid or a pharmacological product including both glucocorticoid and a compound of the invention), the restoration/prevention of dermal atrophy induced by systemic treatment with glucocorticoids, restoration/prevention of atrophy in the respiratory system induced by local treatment with glucocorticoids, UV-induced dermal atrophy, or dermal atrophy induced by aging (wrinkles, etc.), wound healing, keloids, stria, cellulite, roughened skin, actinic skin damage, lichen planus, ichtyosis, acne, psoriasis, Dernier's disease, eczema, atopic dermatitis, chloracne, pityriasis and skin scarring.

In treating skin disorders or diseases as described above, the compounds of the invention may be used in combination with a retinoid or a vitamin D analog.

The compounds of the invention can be administered orally or parenterally such as subcutaneously or intravenously, as well as by nasal application, rectally or sublingually to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, ointment, hydrophilic ointment, cream, lotion, solution or suspension or in other types of carrier of materials such as transdermal devices, iontophoretic devices, rectal suppositories, inhalant devices and the like. The composition or carrier will contain about 5 to about 500 mg per unit of dosage of a compound of formula I. They may be compounded in conventional matter with a physiologically acceptable vehicle or carrier, excipient, binder, preservative, stabilizer, flavor, etc., as called for by accepted pharmaceutical practice.

The following working Examples represent preferred embodiments of the present invention. Appropriate procedures for the preparation of starting materials can be found in: "Novel Thyroid Receptor Ligands and Methods. Li, Yi-Lin; Liu, Ye; Hedfors, Asa; Malm, Johan; Mellin, Charlotta; Zhang, Minsheng. PCT Int. Appl., 40 pp. CODEN: PIXXD2. WO 9900353 A1 990107". The $^1$H NMR spectra was all consistent with the assigned structures.

EXAMPLE 1

3,5-Dimethyl-4-(4-hydroxy-3-isopropylphenoxy)benzyltetrazole

To a stirred solution of 3,5-dimethyl-4-(4-hydroxy-3-isopropylphenoxy)-phenylacetonitrile (154 mg) in 6.3 ml of dimethyl formamide, ammonium chloride (297 mg, 5.21 mmol) and sodium azide (339 mg, 5.21 mmol) was added at reflux. After 4.5 hours the reaction mixture was concentrated, treated with 6 M hydrochloric acid and extracted several times with ethyl acetate. The combined organic phases were dried over magnesium sulphate, filtered and concentrated. The residue was purified by column chromatography (silica gel, 96:4:1 chloroform/methanol/acetic acid) to give 68 mg (37%) of the title compound.

EXAMPLE 2

3,5-Dichloro-4-(4-hydroxy-3-isopropylphenoxy)benzyltetrazole (a) To a stirred solution of 3,5-dichloro-4-(4-methoxy-3-isopropylphenoxy)-phenylacetonitrile (160 mg) in 3.0 ml of dimethyl formamide, ammonium chloride (500 mg) and sodium azide (600 mg) was added at reflux. After 2 hours the reaction mixture was concentrated, treated with 6 M hydrochloric acid and extracted several times with ethyl acetate. The combined organic phases were dried over magnesium sulphate, filtered and concentrated. The residue was purified by column chromatography (silica gel, 96:4:1 chloroform/methanol/acetic acid) to give 60 mg (34%) of 3,5-dichloro-4-(4-methoxy-3-isopropylphenoxy)benzyltetrazole.

(b) A reaction mixture of 3,5-dichloro-4-(4-methoxy-3-isopropylphenoxy)-benzyltetrazole (60 mg), BF$_3$.Me$_2$S (0.5 ml) and CH$_2$Cl$_2$ (6 ml) was stirred at room temperature over night. The yield after purification was quantitative.

EXAMPLES 3–24

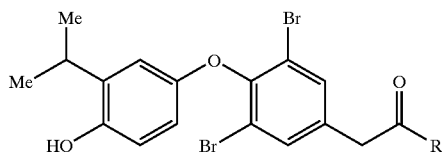

General Procedure

A mixture of 3,5-dibromo-4-(4-hydroxy-3-isopropylphenoxy)phenylacetic acid (222 mg), 3-ethyl-1-[3-(dimethylamino)propyl]carbodiimide hydrochloride (EDCI), (95 mg), 1-hydroxybenzotriazole hydrate (HBT), (91 mg), in dichloromethane (5 ml) was stirred under argon at room temperature for 2 h. In a separate flask, the appropriate amino acid, triethylamine (100 mg) and 5 ml of dichloromethane was stirred for 1 h under N$_2$. The two mixtures were combined and the reaction mixture stirred at 40° C. over night. When the starting carboxylic acid was consumed, the organic phase was removed in vacuo and the residue dissolved in methanol (20 ml) and 1N NaOH (10 ml). The reaction mixture was stirred at 40° C. for 24 h and evaporated. The residue was subjected to semi-preparative HPLC, using gradient elution as outlined below. The amine part "R", and the stereochemistry of the aminoacids is indicated in the table below.

[1]HPLC retention time in minutes and gradient method. Reverse phase HPLC analyses performed on Zorbax-C8-5u-4.6×50 mm analytical columns, flow rate 3 ml/min, detection at 220 nm, and a 10 minute gradient elution by solvent A (10% CH$_3$CN+10 mmol HOOH) and B (CH$_3$CN+10 mmol HOOH). Gradient elution was done in the following way: 0–1 min 90% A, 1–7 min to 100% B, 7–9 min 100% B and 9–10 min return to 10% A. Purification of the Examples were done using a Zorbax-C8-5u-21.5×50 mm semi-preperative column, flow rate 25 ml/min, detection at 220 nm, using the same gradient as for the analytical column. [2]MS result obtained on a PESciEx API150EX using electrospray, both positive and negative ion modes.

| Example | R | Mol Formel | MS m/z (M + H)[1] | HPLC[2] |
|---|---|---|---|---|
| 3 | L-Val | C22H25Br2NO5 | 544.0 | 6.10 |
| 4 | L-Val | C22H25Br2NO5 | 544.0 | 6.07 |
| 5 | L-Tyr | C26H25Br2NO6 | 608.5 | 5.67 |
| 6 | | C23H27Br2NO5 | 558.1 | 6.03 |
| 7 | | C27H27Br2NO5S | 638.2 | 5.49 |
| 8 | D-Leu | C23H27Br2NO5 | 558.1 | 5.38 |
| 9 | D-Tyr | C26H25Br2NO6 | 608.2 | 5.00 |
| 10 | D-Trp | C28H26Br2N2O5 | 631.3 | 5.38 |
| 11 | L-Arg | C23H28Br2N4O5 | 601.3 | 4.54 |
| 12 | L-Abu | C21H23Br2NO5 | 530.2 | 6.22 |
| 13 | | C20H21Br2NO5 | 516.1 | 4.77 |

-continued

| Example | R | Mol Formel | MS m/z (M + H)[1] | HPLC[2] |
|---|---|---|---|---|
| 14 | 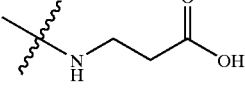 | C20H21Br2NO5 | 516.1 | 4.61 |
| 15 | L-Leu | C23H27Br2NO5 | 558.1 | 5.38 |
| 16 | 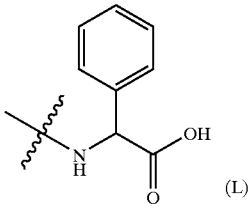 (L) | C25H23Br2NO5 | 578.2 | 5.23 |
| 17 | D-Pro | C22H23Br2NO5 | 542.2 | 4.92 |
| 18 | L-Ile | C23H27Br2NO5 | 558.1 | 5.38 |
| 19 | 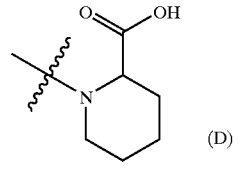 (D) | C23H25Br2NO5 | 556.3 | 5.23 |
| 20 | L-Phe | C26H25Br2NO5 | 592.0 | 5.46 |
| 21 | L-Lys | C23H28Br2N2O5 | 573.1 | 3.77 |
| 22 | 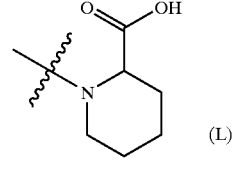 (L) | C23H25Br2NO5 | 556.0 | 5.30 |
| 23 | L-Pro | C22H23Br2NO5 | 542.2 | 4.84 |
| 24 | 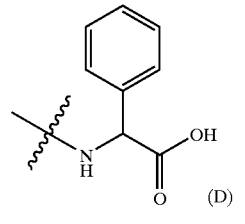 (D) | C25H23Br2NO5 | 578.2 | 5.30 |

EXAMPLE 25

D-N-[3,5-Dibromo-4-(4-hydroxy-3-isopropylphenoxy)phenylacetyl]methionine (a) A solution of 3,5-dibromo-4-(4-hydroxy-3-isopropylphenoxy)phenylacetic acid (222 mg), 3-ethyl-1-[3-(dimethylamino)propyl]carbodiimide hydrochloride (EDCI), (106 mg), 1-hydroxybenzotriazole hydrate (HBT), (101 mg) in dimethyl formamide (5.5 ml) was stirred at room temperature for 0.5 h followed by addition of a solution of D-methionine methyl ester hydrochloride (298 mg) and triethylamine (111 mg) in dimethyl formamide (2.2 ml). After stirring for one hour, the mixture was partitioned between water and chloroform. The organic phase was dried, filtered and concentrated. The residue was subjected to column chromatography (Silica gel, gradient elution with 20% to 40% ethyl acetate in petroleum ether), to give 256 mg (87%) of D-methyl-N-[3,5-dibromo-4-(4-hydroxy-3-isopropylphenoxy)phenylacetyl]methionate. LC-MS (electrospray): m/z 590 (M+H).

(b) D-Methyl-N-[3,5-dibromo-4-(4-hydroxy-3-isopropylphenoxy)phenylacetyl]methionate (88 mg) was hydrolyzed by treatment with 1 M aqueous sodium hydroxide (1 ml) in methanol (2.25 ml), to give 81 mg (94%) of the title compound after column chromatography (Silica gel, gradient elution with chloroform, methanol and acetic acid). LC-MS (electrospray): m/z 574 (M−H).

EXAMPLE 26

L-N-[3,5-Dibromo-4-(4-hydroxy-3-isopropylphenoxy)phenylacetyl]methionine (a) 3,5-Dibromo-4-(4-hydroxy-3-isopropylphenoxy)phenylacetic acid (222 mg) was coupled with D-methionine hydrochloride (298 mg) using the method described in Example 25(a), to give 236 mg (80%) of L-methyl-N-[3,5-dibromo-4-(4-hydroxy-3-isopropylphenoxy)phenylacetyl] methionate after column chromatography. (Silica gel, gradient elution with 20% to 40% ethyl acetate in petroleum ether). LC-MS (electrospray): m/z 590 (M+H).

(b) D-Methyl-N-[3,5-dibromo-4-(4-hydroxy-3-isopropylphenoxy)phenylacetyl]methionate (24 mg) was hydrolyzed using the method described in Example 25(b) to give 20 mg (87%) of the title compound after column chromatography (Silica gel, gradient elution with chloroform, methanol and acetic acid). LC-MS (electrospray): m/z 574 (M−H).

EXAMPLE 27

D-N-[3,5-Dibromo-4-(4-hydroxy-3-isopropylphenoxy)phenylacetyl] α-methylalanine (a) 3,5-Dibromo-4-(4-hydroxy-3-isopropylphenoxy)phenylacetic acid (222 mg) was coupled with D-α-methylalanine hydrochloride (238 mg) using the method described in Example 25(a), to give 269 mg (92%) of D-t-butyl-N-[3,5-dibromo-4-(4-hydroxy-3 isopropylphenoxy)phenylacetyl)] α-methylalanine after column chromatography (Silica gel, gradient elution with 20% to 40% ethyl acetate in petroleum ether). LC-MS (electrospray): m/z 586 (M+H).

(b) D-t-Butyl-N-[3,5-dibromo-4-(4-hydroxy-3-isopropylphenoxy)phenylacetyl] α-methylalanine (88 mg) was was treated with boron tribromide (1 M in dichloromethane. 2.3 ml) at 0° C. The mixture was stirred overnight at room temperature before ice/water was added. The layers were separated and the water layer was extracted with dichloromethane. The combined organic layer was dried, filtered and concentrated, to give 46 mg (58%) of the title compound after column chromatography (Silica gel, gradient elution with chloroform, methanol and acetic acid). LC-MS (electrospray): m/z 528 (M−H).

EXAMPLE 28

D-N-[3,5-Dibromo-4-(4-hydroxy-3-isopropylphenoxy)phenylacetyl]aspargine 3,5-Dibromo-4-(4-hydroxy-3-isopropylphenoxy)phenylacetic acid (444 mg) was mixed with 10 ml thionyl chloride and heated at reflux for 3 h. The reaction mixture was co-evaporated with toluene to give the crude 3,5-dibromo-4-(4-hydroxy-3-isopropylphenoxy)phenylacetyl chloride. N,O-bis(trimethylsilyl)acetamide (670 mg) was added at 0° C., under nitrogen atmosphere, to a mixture of D-Aspargine (225 mg) and 10 ml acetonitrile. The reaction mixture was further stirred at room temperature and a solution of 3,5-dibromo-4-(4-hydroxy-3-isopropylphenoxy)phenylacetyl chloride in 10 ml acetonitrile was added. After stirring for 16 h, the reaction mixture was poured into water and the solid filtered off. The solid was dissolved in methanol and the organic phase removed in vacuo. The residue was purified by HPLC to give 76 mg (14%) of D- N-[3,5-dibromo-4-(4-hydroxy-3-isopropylphenoxy)phenylacetyl]aspargine. LC-MS (electrospray): m/z 557 (M−H).

EXAMPLE 29

L-Methyl-N-[3,5-dibromo-4-(4-hydroxy-3-isopropylphenoxy)phenylacetyl]alanine 3,5-Dibromo-4-(4-hydroxy-3-isopropylphenoxy)phenylacetic acid (200 mg) was coupled with L-methyl alanine hydrochloride (126 mg) using the method described in Example 25(a), to give 140 mg (60%) of the title compound. LC-MS (electrospray): m/z 530 (M+1).

General Procedure for the Preparation of the Amino Acid Library by Solid Phase Synthesis

EXAMPLES 30–55

Loading of the resin with 3,5-dibromo-4-(4-hydroxy-3-isopropylphenoxy benzoic acid A mixture of methyl 3,5-dibromo-4-(4-hydroxy-3-isopropylphenoxy)benzoate (7.6 g, 17.1 mmol), Merrifield resin (5 g, 1.2 mmol/g) and sodium hydride (432 mg, 18 mmol) in 100 ml of dimethyl formamide was stirred in a 250 ml round flask at 50° C. for 40 hours. After cooling, the mixture was filtered and the resin was washed with water (3×10 ml), dimethyl formamide (3×10 ml), ethyl acetate (3×10 ml) and dichloromethane (3×10 ml). The resulting resin was dried in vacuum overnight to give 8.54 g of resin, loaded with the methyl ester.

To the resin was added methanol (100 ml) and an aqueous solution of sodium hydroxide (100 ml, 1 M). The suspension was stirred under at 80° C. for one day, cooled to room temperature and filtered. The resin was washed with water (3×10 ml), tetrahydrofuran (3×10 ml), ethyl acetate (3×10 ml) and dichloromethane (3×10 ml). After drying under vacuum, 5.94 g of resin loaded with the title compound was obtained.

Determination of the Loading Capacity of the Resin:

The resin (100 mg) was treated with a mixture of trifluoroacetic acid, dimethyl sulphite and water (85:15:5). The mixture was stirred at room temperature for two days. The resin was removed by filtration and the organic phase was collected and concentrated under vacuum. The resulting residue was chromatographed on silica gel (methanol/chloroform/acetic acid 10:90:1). The pure fractions were pooled and concentrated affording 17.5 mg (51%) of 3,5-dibromo-4-(4-hydroxy-3-isopropylphenoxy)benzoic acid as white solid. The loading rate was estimated as 0.04 mmol (17,5 mg) per 100 mg of loaded resin.

Coupling of 3,5-dibromo-4-(4-hydroxy-3-isopropylphenoxy) benzoic acid to different amino acids DIVERSOMER® 8–100 synthesizer was used for syntheses and Savant SpeedVac® system for concentration.

To each of eight PINs was added 100 (±5) mg of the loaded resin (17.5 mg/100 mg; 0.04 mmol/100 mg). The resin-filled PINs were placed in the holder block. Eight vials (12 ml) were placed into the reservoir rack, equipped with a magnetic stir bar and filled with a mixture consisting of the corresponding aminoacid ester (0.4 mmol), PyBOP (104 mg, 0.2 mmol), HBT (27 mg, 0.2 mmol), DIEA (52 mg, 0.4 mmol) and dichloromethane (5 ml). The holder block was assembled with the reservoir rack. The reaction was carried out at room temperature with stirring for two days. The reservoir rack was disassembled from the holder block. Each resin in the PINs was dispended with 2 ml each of dimethyl formamide, water, ethyl acetate and dichloromethane. The washing procedure was repeated twice. The resin in PINs was finally dried by pressed air-flow.

Eight new vials (12 ml) were placed into the reservoir rack and each vial was equipped with a magnetic stir bar. The holder block was assembled with the reservoir rack. A methanolic solution of potassium hydroxide (5 ml, 2 M) was in 1 ml increments down through the inside of each PIN. The apparatus was allowed to stand in a fume hood with stirring for two days. The synthesizer was disassembled and the resins were washed with water (4×2 ml), methanol (4×2 ml) and dichloromethane (4×2 ml). The resin in PINs was dried by pressed air-flow.

The holder block was reassembled from the reservoir rack. A 50 ml stock solution of trifluoroacetic acid/dimethyl sulphite/water(85:15:5; v/v) was prepared. The solution (5 ml) was added to each of the eight PINs in 1 ml increments. The apparatus was allowed to stand in a fume hood with stirring for 2 days. The resercoir rack and the holder block was disassembled. Each PIN was washed with 1 ml of the above solution. The contents of the 8 reservoir vials were concentrated to dryness. Each vial was partitioned between aqueous hydrochloric acid (1 ml, 1 M) and ethyl acetate (2 ml). The content of the eight reservoir vials were carefully transferred into the eight drying cartridges (Chem elute CE1003, VARIAN), equipped with test tubes underneath. The cartridges were allowed to drain by gravity, rinsed with ethyl acetate (3×1.5 ml) after 5 min and finally forced to drain under reduced pressure. The organic layer was collected and concentrated to give the following products in the yields mentioned below.

EXAMPLE 30

D-N-[3,5-Dibromo-4-(4-hydroxy-3-isopropylphenoxy)benzoyl]valine 12.2 mg (57.7%)

EXAMPLE 31

D-N-[3,5-Dibromo-4-(4-hydroxy-3-isopropylphenoxy)benzoyl]leucine 20.1 mg (92.5%)

EXAMPLE 32

L-S-Benzyl, N-[3,5-dibromo-4-(4-hydroxy-3-isopropylphenoxy)benzoyl]cysteine 14.9 mg (60%)

EXAMPLE 33

D-N-[3,5-Dibromo-4-(4-hydroxy-3-isopropylphenoxy)benzoyl]tyrosine 5.9 mg (24.8%)

EXAMPLE 34

L-N-δ-(2,2,5,7,8-Pentamethylchroman-6-sulfonyl), N-[3,5-dibromo-4-(4-hydroxy-3-isopropylphenoxy)benzoyl]arginine 10.7 mg (31%)

EXAMPLE 35

L-N-[3,5-Dibromo-4-(4-hydroxy-3-isopropylphenoxy)benzoyl]aminobutyric acid 15.6 mg (75,5%)

EXAMPLE 36

L-N-[3,5-Dibromo-4-(4-hydroxy-3-isopropylphenoxy)benzoyl]valine 19.7 mg (93%)

EXAMPLE 37

L-N-[3,5-Dibromo-4-(4-hydroxy-3-isopropylphenoxy)benzoyl]leucine 14.8 mg (68%)

EXAMPLE 38

L-N-[3,5-Dibromo-4-(4-hydroxy-3-isopropylphenoxy)benzoyl]proline 8.6 mg (41%)

EXAMPLE 39

L-N-[3,5-Dibromo-4-(4-hydroxy-3-isopropylphenoxy)benzoyl]cysteine 2.88 mg (13.5%)

EXAMPLE 40

N-[3,5-Dibromo-4-(4-hydroxy-3-isopropylphenoxy)benzoyl]lysine 15.8 mg (81%)

EXAMPLE 41

L-N-α-[3,5-Dibromo-4-(4-hydroxy-3-isopropylphenoxy)benzoyl]lysine 23.5 mg (105%)

EXAMPLE 42

D-N-α-[3,5-Dibromo-4-(4-hydroxy-3-isopropylphenoxy)benzoyl]lysine 24.9 mg (112%)

EXAMPLE 43

N-[3,5-Dibromo-4-(4-hydroxy-3-isopropylphenoxy)benzoyl]aminoisobutyric acid 6.72 mg (32.6%)

EXAMPLE 44

L-N-[3,5-Dibromo-4-(4-hydroxy-3-isopropylphenoxy)benzoyl]phenylglycine 7.1 mg (31%)

EXAMPLE 45

D-N-[3,5-Dibromo-4-(4-hydroxy-3-isopropylphenoxy)benzoyl]phenylglycine 15.1 mg (67%)

EXAMPLE 46

N-[3,5-Dibromo-4-(4-hydroxy-3-isopropylphenoxy)benzoyl]sarcosine 6.7 mg (33.4%)

EXAMPLE 47

DL-N-[3,5-Dibromo-4-(4-hydroxy-3-isopropylphenoxy)benzoyl]-α-methylphenylalanine 7.4 mg (31.4%)

EXAMPLE 48

L-N-[3,5-Dibromo-4-(4-hydroxy-3-isopropylphenoxy)benzoyl]isoleucine 16.1 mg (70%)

EXAMPLE 49

D-N-[3,5-Dibromo-4-(4-hydroxy-3-isopropylphenoxy)benzoyl]methionine 11.7 mg (52%)

EXAMPLE 50

L-N-[3,5-Dibromo-4-(4-hydroxy-3-isopropylphenoxy)benzoyl]methionine 13.2 mg (58.6%)

EXAMPLE 51

L-N-[3,5-Dibromo-4-(4-hydroxy-3-isopropylphenoxy)benzoyl]phenylalanine 9.7 mg (41.9%)

EXAMPLE 52

D-N-[3,5-Dibromo-4-(4-hydroxy-3-isopropylphenoxy)benzoyl]phenylalanine 12.2 mg (52.9%)

EXAMPLE 53

L-N-[3,5-Dibromo-4-(4-hydroxy-3-isopropylphenoxy)benzoyl]cyclohexylalanine 10.1 mg (43.7%)

EXAMPLE 54

L-N-ε-(Benzyloxycarbonyl), N-α-[3,5-dibromo-4-(4-hydroxy-3-isopropylphenoxy)benzoyl]lysine 10 mg (36%)

EXAMPLE 55

D-N-ε-(Benzyloxycarbonyl), N-α-[3,5-dibromo-4-(4-hydroxy-3-isopropylphenoxy)-benzoyl]lysine 24.4 mg (88%)

EXAMPLE 56

L-N-[3,5-dibromo-4-(4-hydroxy-3-isopropylphenoxy)phenylacetyl]alanine 3,5-Dibromo-4-(4-hydroxy-3-isopropylphenoxy)phenylacetic acid (200 mg) was coupled with L-methyl alanine hydrochloride (126 mg) using the method described in Example 25(a) and subsequently hydrolyzed using the method described in Example 25(b). The crude mixture was purified by semi-preparative HPLC, to give 40 mg (21%) of L-N-[3,5-dibromo-4-(4-hydroxy-3-isopropylphenoxy)phenylacetyl]alanine. LC-MS (electrospray): m/z 516 (M+H).

EXAMPLE 57

L-Dimethyl-N-[3,5-dibromo-4-(4-hydroxy-3-isopropylphenoxy)phenylacetyl]glutamate 3,5-Dibromo-4-(4-hydroxy-3-isopropylphenoxy)phenylacetic acid (200 mg) was coupled with L-dimethyl glutamate hydrochloride (190 mg) using the method described in Example 25(a). The crude mixture was purified by semi-preparative HPLC to give 150 mg (55%) of the title compound. LC-MS (electrospray): m/z 601 (M+1).

EXAMPLE 58

3,5-Dibromo-4-(4-hydroxy-3-isopropylphenoxy)benzoyl-5-hydroxy-1-naphthalenesulphonamide To a stirred mixture of 5-hydroxy-1-naphthalenesulphonamide (0.175 mmol) in dichloromethane (0.2 ml) was added a solution of 3,5-dibromo-4-(4-hydroxy-3-isopropylphenoxy)benzoic acid (0.035 mmol), DIEA (0.175 mmol) and dichloromethane (0.2 ml), dimethyl formamide was added to the solution if the sulphonamide not dissolved completely in dichloromethane. After 15 minutes PyBOP (0.042 mmol) and HOBt (0.001 mmol) in dichloromethane (0.3 ml) was added. The reaction mixture was heated at 50° C. for 20 hours. After cooling to room temperature, dichloromethane (1 ml) and citric acid solution (5%, 1 ml) was added and stirred vigorously for 30 min. The organic phase was dried, concentrated and the residue was finally subjected to semi-preparative HPLC (Silica column: 250×20 mm, ethyl acetate/n-heptane (both with 0.5% acetic acid). Gradient: first 2 min 15% ethyl acetate, then over 13 min to 100% ethyl acetate, then additional 5 min 100% ethyl acetate) to give 12 mg (54%) of the title compound.

EXAMPLE 59

3,5-Dibromo-4-(4-hydroxy-3-isopropylphenoxy)benzoyl-4-toluenesulphonamide 3,5-Dibromo-4-(4-methoxy-3-isopropylphenoxy)benzoic acid (0.035 mmol) was coupled with toluenesulphonamide (0.175 mmol) using the method described in Example 58. Purification on HPLC of the residue gave 14 mg (69%) of the title compound.

EXAMPLE 60

3,5-Dibromo-4-(4-hydroxy-3-isopropylphenoxy)benzoyl-4-nitrobenzenesulphonamide 3,5-Dibromo-4-(4-methoxy-3-isopropylphenoxy)benzoic acid (, 0.035 mmol) was coupled with 4-nitrophenylsulfonamid (0.175 mmol) using the method described in Example 58. Purification on HPLC of the residue gave 8 mg (37%) of the title compound.

EXAMPLE 61

3,5-Dibromo-4-(4-hydroxy-3-isopropylphenoxy) benzoyl sulfamide 3,5-Dibromo-4-(4-methoxy-3-isopropylphenoxy)benzoic acid (0.035 mmol) was coupled with sulfamide (0.175 mmol) using the method described in Example 58. Purification on HPLC of the residue gave 13 mg (73%) of the title compound.

EXAMPLE 62

3,5-Dibromo-4-(4-hdroxy-3-isopropylphenoxy)benzoyl-5-dimethylamino-1-naphthalene-sulphonamide 3,5-Dibromo-4-(4-methoxy-3-isopropylphenoxy)benzoic acid (0.035 mmol) was coupled with 5-dimethylamino-1-naphthalenesulphonamide (0.175 mmol) using the method described in Example 58. Purification on HPLC of the residue gave 8 mg (34%) of the title compound.

EXAMPLE 63

3,5-Dibromo-4-(4-hydroxy-3-isopropylphenoxy)benzoyl-4-aminobenzenesulphonamide 3,5-Dibromo-4-(4-methoxy-3-isopropylphenoxy)benzoic acid (0.035 mmol) was coupled with 4-aminobenzenesulphonamide (0.175 mmol) using the method described in Example 58. Purification on HPLC of the residue gave 7 mg (34%) of the title compound.

EXAMPLE 64

Methyl-[[3,5-Dibromo-4-(4-hydroxy-3-isopropylphenoxy)benzoyl-2-sulphonamide] benzoate 3,5-Dibromo-4-(4-methoxy-3-isopropylphenoxy)benzoic acid (0.035 mmol) was coupled with methyl 2-sulphonamide benzoate (0.175 mmol) using the method described in Example 58. Purification on HPLC of the residue gave 12 mg (55%) of the title compound.

EXAMPLE 65

3,5-Dibromo-4-(4-hydroxy-3-isopropylphenoxy)benzol-2-aminobenzenesulphonamide 3,5-Dibromo-4-(4-methoxy-3-isopropylphenoxy)benzoic acid (0.035 mmol) was coupled with 2-aminobenzenesulphonamide (0.175 mmol) using the method described in Example 58. Purification on HPLC of the residue gave 11 mg (54%) of the title compound.

EXAMPLE 66

3,5-Dibromo-4-(4-hydroxy-3-isopropylphenoxy)benzoyl-2-toluenesulphonamide 3,5-Dibromo-4-(4-methoxy-3-isopropylphenoxy)benzoic acid (0.035 mmol) was coupled with 2-toluenesulphonamide (0.175 mmol) using the method described in Example 58. Purification on HPLC of the residue gave 15 mg (74%) of the title compound.

EXAMPLE 67

3,5-Dibromo-4-(4-hydroxy-3-isopropylphenoxy) benzoyl-4-(2-aminoethyl)benzenesulphonamide 3,5-Dibromo-4-(4-methoxy-3-isopropylphenoxy)benzoic acid (0.035 mmol) was coupled with 4-(2-aminoethyl)benzenesulphonamide (0.175 mmol) using the method described in Example 58. Purification on HPLC of the residue gave 10 mg (47%) of the title compound.

EXAMPLE 68

3,5-Dibromo-4-(4-hydroxy-3-isopropylphenoxy) benzoyl-4-(2-aminomethyl)benzenesulphonamide 3,5-Dibromo-4-(4-methoxy-3-isopropylphenoxy)benzoic acid (, 0.035 mmol) was coupled with 4-(2-aminomethyl)benzenesulphonamide (0.175 mmol) using the method described in Example 58. Purification on HPLC of the residue gave 16 mg (76%) of the title compound.

EXAMPLE 69

3,5-Dibromo-4-(4-hydroxy-3-isopropylphenoxy)benzoyl-3-nitrobenzenesulphonamide 3,5-Dibromo-4-(4-methoxy-3-isopropylphenoxy)benzoic acid (0.035 mmol) was coupled with 3-nitrobenzenesulphonamide (0.175 mmol) using the method described in Example 58. Purification on HPLC of the residue gave 7 mg (33%) of the title compound.

EXAMPLE 70

3,5-Dibromo-4-(4-hydroxy-3-isopropylphenoxy)benzoyl-4-chlorobenzenesulphonamide 3,5-Dibromo-4-(4-methoxy-3-isopropylphenoxy)benzoic acid (0.035 mmol) was coupled with 4-chlorobenzenesulphonamide (0.175 mmol) using the method described in Example 58. Purification on HPLC of the residue gave 13 mg (62%) of the title compound.

EXAMPLE 71

L-Dimethyl-N-[3,5-dibromo-4-(4-hydroxy-3-isopropylphenoxy)phenylacetyl]glutamate 3,5-Dibromo-4-(4-hydroxy-3-isopropylphenoxy)phenylacetic acid (200 mg) was coupled with L-dimethyl glutamate hydrochloride (190 mg) using the method described in Example 25(a). The crude mixture was purified by semi-preparative HPLC, to give 150 mg (55%) of the title compound. LC-MS (electrospray): m/z 601 (M+H).

EXAMPLE 72

L-(O-tert-butyl)methyl-N-[3,5-dibromo-4-(4-hydroxy-3-isopropylphenoxy)phenylacetyl]glutamate 3,5-Dibromo-4-(4-hydroxy-3-isopropylphenoxy)phenylacetic acid (200 mg) was coupled with L-(O-tertbuthyl) methyl glutamate hydrochloride (228 mg) using the method described in Example 25(a). The crude mixture was purified by semi-preparative HPLC, to give 70 mg (24%) of the title compound. LC-MS (electrospray): m/z 643 (M+H).

EXAMPLE 73

L-N-[3,5-dibromo-4-(4-hydroxy-3-isopropylphenoxy)phenylacetyl]glutamic acid 3,5-Dibromo-4-(4-hydroxy-3-isopropylphenoxy)phenylacetic acid (200 mg) was coupled with L-dimethyl glutamate hydrochloride (190 mg) using the method described in Example 25(a) and subsequently hydrolyzed using the method described in Example 25(b). The crude mixture was purified by semi-preparative HPLC, to give 62 mg (31%) of the title compound. LC-MS (electrospray): m/z 574 (M+H).

EXAMPLE 74

L-N-[3,5-Dichloro-4-(4-hydroxy-3-isopropylphenoxy)phenylacetyl]aspartic acid (a) A solution of 3,5-dichloro-4-(4-hydroxy-3-isopropylphenoxy)phenylacetic acid (50 mg), 3-ethyl-1-[3-(dimethylamino)propyl]carbodiimide hydrochloride (EDCI), (30 mg), 1-hydroxybenzotriazole hydrate (HBT), (28 mg) in dimethyl formamide (1 ml) was stirred at room temperature for 0.5 h followed by addition of a solution of L-di-t-butyl aspartate hydrochloride (52 mg) and triethylamine (32 mg) in dimethyl formamide (1 ml). After stirring for three days, the mixture was partitioned between water and ethyl acetate. The organic phase was washed with brine and then dried, filtered and concentrated. The residue was chromatographed on silica gel eluted with ethyl acetate/light petroleum ether (1:4). Pure fractions were pooled and concentrated to give L-di-t-butyl N-[3,5-dichloro-4 (4-hydroxy-3-isopropylphenoxy)phenylacetyl]aspartate (68 mg, 83%).

(b) The above ester (48 mg) was hydrolyzed using the method described in Example 25(b) to give L-N-[3,5-dichloro-4-(4-hydroxy-3-isopropylphenoxy)phenylacetyl] aspartic acid (27 mg, 70%).

EXAMPLE 75

D-di-tert-butyl-N-[3,5-dibromo-4-(4-hydroxy-3-isopropylphenoxy)phenylacetyl]glutamate 3,5-Dibromo-4-(4-hydroxy-3-isopropylphenoxy)phenylacetic acid (200 mg) was coupled with D-ditertbutyl glutamate hydrochloride (266 mg) using the method described in Example 25(a). The crude mixture was purified by semi-preparative HPLC, to give 170 mg (70%) of the title compound. LC-MS (electrospray): m/z 685 (M+H).

EXAMPLE 76

D-N-[3,5-Dibromo-4-(4-hydroxy-3-isopropylphenoxy)phenylacetyl]glutamic acid 3,5-Dibromo-4-(4-hydroxy-3-isopropylphenoxy)phenylacetic acid (200 mg) was coupled with D-di-tert-butyl glutamate hydrochloride (190 mg) using the method described in Example 25(a) and subsequently hydrolyzed using the method described in Example 25(b). The crude mixture was purified by semi-preparative HPLC, to give 60 mg (23%) of the title compound. LC-MS (electrospray): m/z 574 (M+H).

EXAMPLE 77

L-O-tert-Butyl-N-[3,5-dibromo-4-(4-hydroxy-3-isopropylphenoxy)phenylacetyl]glutamine 3,5-Dibromo-4-(4-hydroxy-3-isopropylphenoxy)phenylacetic acid (200 mg) was coupled with L-O-tert-buthyl glutamine hydrochloride (230 mg) using the method described in Example 25(a). The crude mixture was purified by semi-preparative HPLC, to give 100 mg (44%) of the title compound. LC-MS (electrospray): m/z 629 (M+H).

EXAMPLE 78

L-N-[3,5-Dibromo-4-(4-hydroxy-3-isopropylphenoxy)phenylacetyl]glutamine 3,5-Dibromo-4-(4-hydroxy-3-isopropylphenoxy)phenylacetic acid (200 mg) was coupled with L-tert-butyl glutamine hydrochloride (230 mg) using the method described in Example 25(a) and subsequently hydrolyzed using the method described in Example 25(b). The crude mixture was purified by semi-preparative HPLC, to give 40 mg (15%) of the title compound. LC-MS (elctrospray): m/z 574 (M+H).

EXAMPLE 79

D-N-[3,5-Dibromo-4-(4-hydroxy-3-isopropylphenoxy)phenylacetyl]glutamine 3,5-Dibromo-4-(4-hydroxy-3-isopropylphenoxy)phenylacetic acid (200 mg) was coupled with D-glutamine hydrochloride (163 mg) using the method described in Example 25(a) and subsequently hydrolyzed using the method described in Example 25(b). The reaction mixture was concentrated in vacuo. The residue was subjected to semi-preparative HPLC, to give 30 mg (12%) of the title compound. LC-MS (electrospray): m/z 574 (M+H).

EXAMPLE 80

L-O-Benzyl-N-[3,5-dibromo-4-(4-hydroxy-3-isopropylphenoxy)phenylacetyl]aspartic acid 3,5-Dibromo-4-(4-hydroxy-3-isopropylphenoxy)phenylacetic acid (200 mg) was coupled with L-O-Benzyl aspartic acid (266 mg) using the method described in Example 25(a). The crude mixture was purified by semi-preparative HPLC, to give 140 mg (38%) of the title compound. LC-MS (electrospray): m/z 650 (M+1).

EXAMPLE 81

L-O-tert-Butyl-N-[3,5-dibromo-4-(4-hydroxy-3-isopropylphenoxy)phenylacetyl]asparagine 3,5-Dibromo-4-(4-hydroxy-3-isopropylphenoxy)phenylacetic acid (200 mg) was coupled with L-O-tert-butyl asparagine hydrochloride (170 mg) using the method described in Example 25(a). The crude mixture was purified by HPLC, to give 40 mg (16%) of the title compound. LC-MS (electrospray): m/z 558 (M+H).

EXAMPLE 82

L-Methyl-N-[3,5-dibromo-4-(4-hydroxy-3-isopropylphenoxy)phenylacetyl]homoserine 3,5-Dibromo-4-(4-methoxy-3-isopropylphenoxy)phenylacetic acid (134 mg) was coupled with L-homoserine (36 mg) using the method described in Example 25(a). The crude residue was dissolved in MeOH and heated at reflux with $SOCl_2$ for 2 h. After evaporaton of the solvent, the residue was chromatographed on column (silica gel, $CHCl_3$/MeOH 97:3). Pure fractions were pooled and concentrated to give 100 mg (64%) of the title compound.

EXAMPLE 83

L-N-[3,5-Dibromo-4-(4-hydroxy-3-isopropylphenoxy)phenylacetyl]homoserine

L-Methyl-N-[3,5-dibromo-4-(4-hydroxy-3-isopropylphenoxy)phenylacetyl]homoserine (100 mg) was hydrolyzed using the method described in Example 25(b). The crude product was purified by HPLC to give 30 mg (30%) of L-N-[3,5-dibromo-4-(4-hydroxy-3-isopropyl-phenoxy)phenylacetyl]homoserine

EXAMPLE 84

D-Methyl-N-[3,5-dibromo-4-(4-hydroxy-3-isopropylphenoxy)phenylacetyl]homoserine 3,5-Dibromo-4-(4-methoxy-3-isopropylphenoxy)phenylacetic acid (140 mg) was coupled with L-homoserine (36 mg) and re-esterified using the method described in Example 82. This gave 100 mg (64%) of D-methyl-N-[3,5-dibromo-4-(4-hydroxy-3-isopropylphenoxy)phenylacetyl]homoserine.

EXAMPLE 85

D-N-[3,5-Dibromo-4-(4-hydroxy-3-isopropylphenoxy)phenylacetyl]homoserine

D-Methyl-N-[3,5-dibromo-4-(4-hydroxy-3-isopropylphenoxy)phenylacetyl]homoserine (100 mg) was hydrolyzed using the method described in Example 25(b). The crude product was purified by HPLC to give 30 mg (30%) of D-N-[3,5-dibromo-4-(4-hydroxy-3-isopropyl-phenoxy)phenylacetyl]homoserine.

EXAMPLE 86

N-[3,5-Dichloro-4-(4-hydroxy-3-isopropylphenoxy)benzoyl]glycine (a) A stirred mixture of 3,5-dichloro-4-(4-hydroxy-3-isopropylphenoxy)benzoic acid (9.56 g, 28.02 mmol), methyl glycine ester hydrochloride (5.28 g, 42.05 mmol), 1-[3-(dimethylamino)propyl]-3-ethylcarbodiimide hydrochloride (6.45 g, 33.64 mmol), 1-hydroxybenzotriazole (4.54 g, 33.60 mmol), $CH_2Cl_2$ (260 mL) and DMF (20 mL) was cooled with an ice-$H_2O$ bath. N-methylmorpholine (5.7 g, 6.2 mL. 56.35 mmol) was added under $N_2$ and the reaction mixture was allowed to attain room temperature. After 18 h, $CH_2Cl_2$ was removed in vacuo and the residue partionated beetween EtOAc (300 mL) and $H_2O$ (150 mL). The organic phase was successively washed with 1N HCl (2×150 mL), saturated aqueous $NaHCO_3$ (2×150 mL), and brine (2×150 mL). The organic phase was dried ($Na_2SO_4$), filtered and concentrated in vacuo to give 11.5 g of crude product as an orange solid. The crude product was purified by chromatography (Silica gel, 40% EtOAc in hexane) to give 9.76 g (84% yield) of slightly yellowish solid. $^1H$ NMR (500 MHz, $CDCl_3$): δ7.82 (s, 2H), 6.78 (d, 1H, J=2.7 Hz), 6.63 (d, 1H, J=8.8 Hz), 6.61 (t, 1H, J=4.9 Hz), 6.38 (dd, 1H, J=8.8, 3.3 Hz), 4.65 (s, 1H), 4.24 (d, 2H, J=5 Hz), 3.82 (s, 3H), 3.16 (heptet, 1H, 6.6 Hz), 1.22 (d, 6H, J=6.6 Hz); $^3C$ NMR: δ 170.18, 164.65, 150.66, 148.36, 136.26, 131.63, 130.57, 128.10, 115.76, 113.94, 112.28, 52.69, 41.87, 27.34, 22.38; MS-ESI$^{31}$ [M−H]$^{31}$ =410, 412, 414 (100:64:10).

(b) To a solution of methyl N-[3,5-dichloro-4-(4-hydroxy-3-isopropylphenoxy)benzoyl] glycinate (7.30 g, 17.71 mmol) in THF (106 mL) was added 1 N aqueous lithium hydroxide solution (53 mL, 53 mmol). After 2h, the mixture was acidified with 1 N HCl and extracted with EtOAc (200 mL). The organic phase was washed with brine (2×75 mL), dried ($Na_2SO_4$), filtered and concentrated in vacuo. The concentrate was triturated with $CH_2Cl_2$(100 mL) and the white solid material obtained was dried in vacuo to give 6.85 g of the title product (97% yield). $^1H$ NMR (500 MHz, $CD_3OD$): δ 7.82 (s, 2H), 6.78 (d, 1H, J=2.7 Hz), 6.63 (d, 1H, J=8.8 Hz), 6.61 (t, 1H, J=4.9 Hz), 6.38 (dd, 1H, J=8.8, 3.3 Hz), 4.65 (s, 1H), 4.24 (d, 2H, J=5 Hz), 3.16 (heptet, 1H, 6.6 Hz), 1.22 (d, 6H, J=6.6 Hz); $^{13}C$ NMR: δ 172.88, 167.20, 151.81, 151.34, 151.13, 137.67, 133.40, 131.39, 129.63, 116.41, 114.19, 113.28, 42.27, 28.19, 22.85; MS-ESI$^-$ [M−H]$^-$=396, 398, 400 (100:64:10).

EXAMPLE 87

N-[3,5-Dichloro-4-(4-hydroxy-3-isopropylphenoxy)benzoyl]sarcosine (a) To a solution of 3,5-dichloro-4-(4-methoxy-3-isopropylphenoxy)benzoic acid (60 mg, 0.169 mmol) in $CH_2Cl_2$ (10 mL) cooled with an ice-$H_2O$ bath was added sarcosine methyl ester hydrochloride (35.4 mg, 0.253 mmol), 1-[3-(dimethylamino)propyl]-3-ethylcarbodiimide hydrochloride (38.9 mg, 0.203 mmol) and 1-hydroxy-7-azabenzotriazole (27.6 mg, 0.203 mmol) and N-methylmorpholine (34.2 mg, 37 uL, 0.338 mmol). The mixture was allowed to warn up to RT and left to stir overnight (ca. 18h). The mixture was taken up in EtOAc (50 mL) and $H_2O$ (20 mL). The organic layer was separated and then it was washed successively with 1N HCl (2×25 mL), saturated $NaHCO_3$ aqueous solution (2×25 mL) and brine (2×25 mL). The organic extract was dried ($Na_2SO_4$), filtered and concentrated in vacuo. The crude product was purified by chromatography (25 g silica gel. 30% EtOAc in hexane) to give 41 mg of purified material (55% yield). Satisfactory proton and LC-MS were obtained.

(b) To a solution of the product above (30 mg, 0.068 mmol) in anhydrous $CH_2Cl_2$ (3 mL) cooled with an ice-$H_2O$ bath was added boron tribromide (0.7 mL, 1.0 M in $CH_2Cl_2$, 0.7 mmol). After 2h, the mixture was poured into ice-$H_2O$ (25 mL). After 15 min of stirring, the product was extracted with EtOAc (50 mL). The organic extract was washed with brine (2×25 mL), dried ($MgSO_4$), filtered and concentrated in vacuo. The crude product, a mixture of free acid and methyl ester, was dissolved in THF (2 mL) and 1N lithium hydroxide aqueous solution (1 mL) was added. After an hour, the mixture was acidified with 1N HCl and then extracted with EtOAc (25 mL). The EtOAc extract was washed with brine (2×15 mL), dried ($Na_2SO_4$), filtered and concentrated in vacuo to give 35 mg of crude product. The crude product was purified by prep HPLC to give 12.3 mg of slightly yellowish solid as purified material (44% yield). Satisfactory proton and mass spectra were obtained.

EXAMPLE 88

3,5-Dibromo-4-(4-hydroxy-3-isopropylphenoxy)phenylacetyl-5-dimethylamino-1-naphthalenesulphonamide To a solution of the 3,5-dibromo-4-(4-hydroxy-3-isopropylphenoxy)phenylacetic acid (50 mg, 0.09 mmol), dimethylaminopyridine (4 mg, 0.018 mmol) and 5-dimethylamino]-naphthalenesulphonamide (45 mg, 0.18 mmol) in 50% dichloromethane in dimethyl formamide (0.2 ml) was added a solution of 1-(3-dimethylaminopropyl)-3-ethylcarbodiimide hydrochloride (28 mg, 0.13 mmol) and diisopropylethyl amine (17 mg, 0.13 mmol) in 50% methylene chloride in dimethyl formamide (0.2 ml). The reaction mixture was vortexed and allowed to stand at room temperature for 6 hours. A solution of ammonium fluoride (0.5 M in methanol; 0.4 ml) was added. After 16 hours, the reaction mixture was evaporated to dryness, re-dissolved in a solvent mixture containing 90% methanol, 10% water and 0.1% trifluoroacetic acid (2 ml) and purified by preparative HPLC (YMC S5 ODS 30×250 mm: 50–100% solvent B in 30 min: solvent A—90% water, 10% methanol, 0.1% trifluoroacetic acid; solvent B—10% water, 90% methanol, 0.1% trifluoroacetic acid: flow rate 25 ml per min: detection 220 nm). The yield was 10.1 mg (16%).

EXAMPLE 89–91

These compounds were prepared and purified in a similar manner as above. For a table of Examples 88–91 comprising the coupled sulphonamide, retention times and mass spectra, see Scheme below.

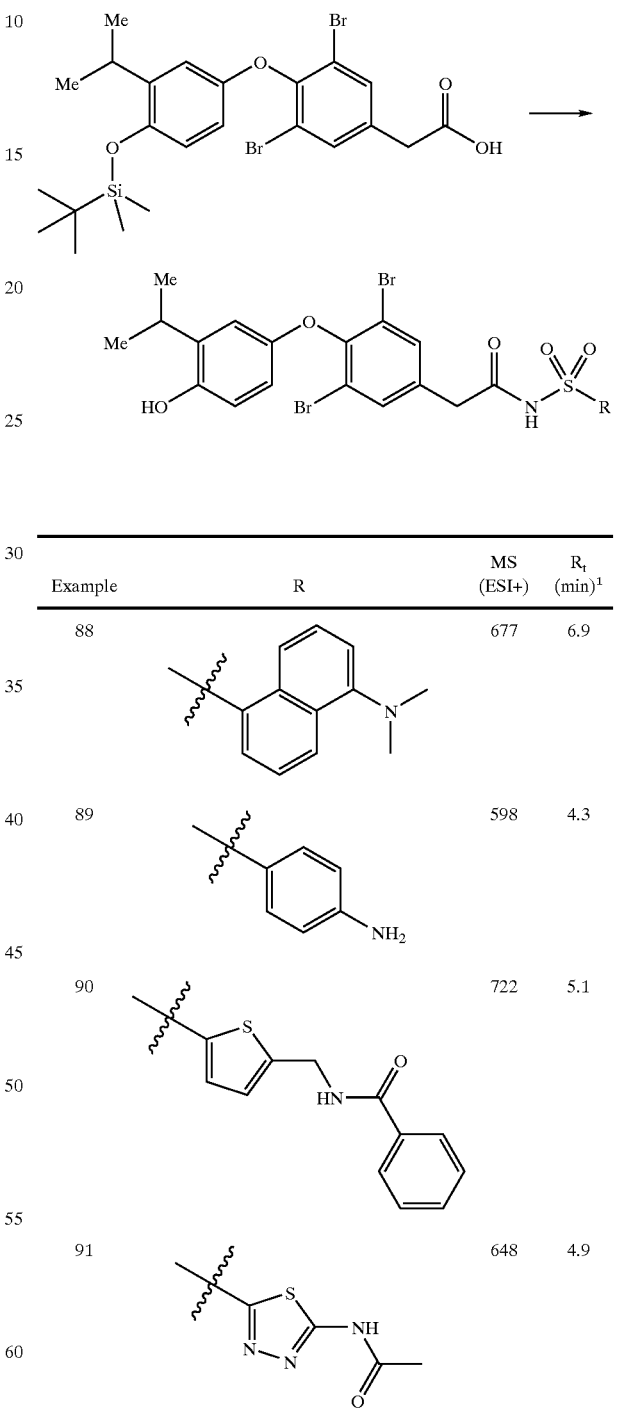

| Example | R | MS (ESI+) | $R_t$ (min)[1] |
|---|---|---|---|
| 88 | | 677 | 6.9 |
| 89 | | 598 | 4.3 |
| 90 | | 722 | 5.1 |
| 91 | | 648 | 4.9 |

[1] YMC ODS 4.6 × 50 mm: 50–100% solvent B in 8 min: solvent A - 90% water, 10% methanol, 0.2% phosphoric acid; solvent B - 10% water, 90% methanol, 0.2% phosphoric acid: flow rate 2.5 ml per min: detection 220 nm

EXAMPLES 92–191

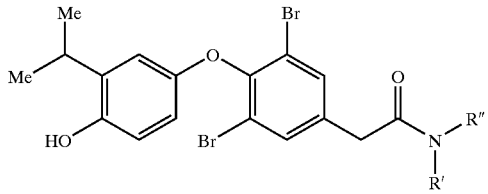

Procedures for the synthesis of the library compounds indicated in the Table below are described in Lawrence, R. M.; Biller, S. A.; Fryszman, O. M.; Poss, M. A. *Synthesis* 1997, 553.

[1]HPLC retention time in minutes and gradient method. Reverse phase HPLC analyses performed on YMC S5 ODS 4.6×50 mm analytical columns, detection at 220 mm and 4 minute gradient elutions by either: method a, 0% B, 1100% A to 1100% B, 0% A; or method b, 20% B, 80% A to 100% B, 0% A, where solvent A is 90% water, 10% methanol, 0.2% phosphoric acid and solvent B is 10% water, 90% methanol, 0.2% phosphoric acid. [2]MS result obtained on a Micromass Platform II using electrospray, both positive and negative ion modes.

[3]Method A examples were prepared by synthesis procedure A in the reference cited above. In these examples, a second basic nitrogen is present in the amine coupling partner. However, only one nitrogen is capable of giving the normal acylation product. Method B examples were prepared by procedure C in the reference cited above.

| Example | —NR'R" | HPLC[1] | MS[2] | Formula | Method[3] |
|---|---|---|---|---|---|
| 92 | 3-(AMINOMETHYL)PYRIDINE | 2.76,a | m/z 534.84 (M + H) | C23H22Br2N2O3 | A |
| 93 | 2-(2-AMINOETHYL)PYRIDINE | 2.73,a | m/z 548.83 (M + H) | C24H24Br2N2O3 | A |
| 94 | 3-(2-AMINOETHYL)PYRIDINE | 2.73,a | m/z 548.82 (M + H) | C24H24Br2N2O3 | A |
| 95 | 2-(AMINOMETHYL)PYRIDINE | 2.84,a | m/z 534.85 (M + H) | C24H3OBr2N2O3 | A |
| 96 | 4-(AMINOMETHYL)PYRIDINE | 2.74,a | m/z 534.82 (M + H) | C24H3OBr2N2O3 | A |
| 97 | 1-(4-METHOXYPHENYL)PIPERAZINE DIHYDROCHLORIDE | 3.33,a | m/z 618.81 (M + H) | C29H32Br2N2O3 | A |
| 98 | 1-(2-FLUOROPHENYL)PIPERAZINE | 3.53,a | m/z 607.16 (M + H) | C34H32Br2N2O3 | A |
| 99 | 2-(2-(AMINOMETHYL)PHENYLTHIO)BENZYL ALCOHOL | 4.42,a | m/z 671.97 (M + H) | C31H29Br2NO4S | B |
| 100 | 2-(1-CYCLOHEXENYL)ETHYLAMINE | 4.56,a | m/z 551.98 (M + H) | C25H29Br2NO3 | B |
| 101 | 2-AMINOINDAN | 4.44,a | m/z 559.88 (M + H) | C26H25Br2NO3 | B |
| 102 | 2-AMINOMETHYLBENZODIOXAN | 4.39,a | m/z 591.93 (M + H) | C26H25Br2NO5 | B |
| 103 | 3-PHENYL-1-PROPYLAMINE | 4.44,a | m/z 560.00 (M + H) | C26H27Br2NO3 | B |
| 104 | 2-(P-TOLYL)ETHYLAMINE | 4.48,a | m/z 559.95 (M + H) | C26H27Br2NO3 | B |
| 105 | 1-(3-AMINOPROPYL)-2-PYRROLIDINONE | 3.97,a | m/z 568.97 (M + H) | C24H28Br2N2O4 | B |
| 106 | BETA-ALANINE 4-METHOXY-BETA-NAPHTHYLAMIDE | 4.52,a | m/z 670.88 (M + H) | C31H30Br2N2O5 | B |
| 107 | 2-CHLOROBENZYLAMINE | 4.38,a | m/z 612.98 (M +?) | C24H22Br2ClNO3 | B |
| 108 | 2-AMINOMETHYL-3-CHLORODIPHENYLETHER | 4.65,a | m/z 660.08 (M + H) | C3OH26Br2ClNO4 | B |
| 109 | DL-ALPHA-AMINO-EPSILON-CAPROLACTAM | 4.03,a | m/z 554.86 (M + H) | C23H26Br2N2O4 | B |
| 110 | L-PHENYLALANINOL | 4.22,a | m/z 577.92 (M + H) | C26H27Br2NO4 | B |
| 111 | 4-(1,2,3-THIADIAZOL-4-YL)BENZYLAMINE | 4.21,a | m/z 617.69 (M + H) | C26H23Br2N3O3S | B |
| 112 | 2-AMINOMETHYLTHIOPHENE | 4.21,a | m/z 539.84 (M + H) | C22H21Br2NO3S | B |
| 113 | 1-(1-NAPHTHYL)ETHYLAMINE | 4.54,a | m/z 597.83 (M + H) | C29H27Br2NO3 | B |
| 114 | 3-CHLORO-4-METHYLBENZYLAMINE | 4.53,a | m/z 581.80 (M + H) | C25H24Br2ClNO3 | B |
| 115 | TETRAHYDROFURFURYLAMINE | 4.07,a | m/z 527.90 (M + H) | C22H25Br2NO4 | B |
| 116 | 2,4-DICHLOROPHENETHYLAMINE | 4.66,a | m/z 615.73 (M + H) | C25H23Br2Cl2NO3 | B |
| 117 | ETHYL 4-AMINO-1-PIPERIDINECARBOXYLATE | 4.21,a | m/z 599.05 (M + H) | C25H30Br2N2O5 | B |
| 118 | 2,6-DIFLUOROBENZYLAMINE | 4.25,a | m/z 569.82 (M + H) | C24H21Br2F2NO3 | B |
| 119 | 2-IODOBENZYLAMINE | 4.46,a | m/z 659.45 (M + H) | C24H22Br2INO3 | B |
| 120 | 2-METHYLBENZYLAMINE | 4.38,a | m/z 547.89 (M + H) | C25H25Br2NO3 | B |
| 121 | BENZYLAMINE | 4.27,a | m/z 533.85 (M + H) | C24H23Br2NO3 | B |
| 122 | 3-METHYLBENZYLAMINE | 4.38,a | m/z 547.89 (M + H) | C25H25Br2NO3 | B |
| 123 | 2-METHOXYPHENETHYLAMINE | 4.41,a | m/z 577.81 (M + H) | C26H27Br2NO4 | B |
| 124 | 3-METHOXYPHENETHYLAMINE | 4.35,a | m/z 577.87 (M + H) | C26H27Br2NO4 | B |
| 125 | 2-ETHOXYBENZYLAMINE | 4.42,a | m/z 577.86 (M + H) | C26H27Br2NO4 | B |
| 126 | (R)-(–)-1-CYCLOHEXYLETHYLAMINE | 4.56,a | m/z 553.90 (M + H) | C25H31Br2NO3 | B |
| 127 | 4-METHOXYPHENETHYLAMINE | 4.32,a | m/z 577.83 (M + H) | C26H27Br2NO4 | B |
| 128 | 2-FLUOROBENZYLAMINE | 4.27,a | m/z 551.85 (M + H) | C24H22Br2FNO3 | B |
| 129 | 2-CHLORO-6-METHYLBENZYLAMINE | 4.48,a | m/z 581.85 (M + H) | C25H24Br2ClNO3 | B |
| 130 | 4-CHLOROBENZYLAMINE | 4.42,a | m/z 567.83 (M + H) | C24H22Br2ClNO3 | B |
| 131 | BETA-METHYLPHENETHYLAMINE | 4.43,a | m/z 561.88 (M + H) | C26H27Br2NO3 | B |
| 132 | 1,1-DI(P-ANISYL)METHYLAMINE | 4.47,a | m/z 669.88 (M + H) | C32H31Br2NO5 | B |
| 133 | MAYBRIDGE BTB 12133 | 4.18,a | m/z 623.84 (M + H) | C27H29Br2NO6 | B |

-continued

| Example | —NR'R" | HPLC[1] | MS[2] | Formula | Method[3] |
|---|---|---|---|---|---|
| 134 | DL-2-AMINO-1-PENTANOL | 4.12,a | m/z 529.91 (M + H) | C22H27Br2NO4 | B |
| 135 | L-PHENYLALANINE P-NITROANILIDE | 4.56,a | m/z 711.88 (M + H) | C32H29Br2N3O6 | B |
| 136 | ETHYL 3-AMINOBUTYRATE | 4.16,a | m/z 557.85 (M + H) | C23H27Br2NO5 | B |
| 137 | (1S,2R)-(+)-2-AMINO-1,2-DIPHENYLETHANOL | 4.28,a | m/z 639.92 (M + H) | C31H29Br2NO4 | B |
| 138 | 2-FLUOROPHENETHYLAMINE | 4.37,a | m/z 565.90 (M + H) | C25H24Br2FNO3 | B |
| 139 | 2-ETHYLHEXYLAMINE | 4.70,a | m/z 555.93 (M + H) | C25H33Br2NO3 | B |
| 140 | 3-FLUOROPHENETHYLAMINE | 4.36,a | m/z 565.85 (M + H) | C25H24Br2FNO3 | B |
| 141 | (1S,2S)-(+)-2-AMINO-3-METHOXY-1-PHENYL-1-PROPANOL | 4.19,a | m/z 607.89 (M + H) | C27H29Br2NO5 | B |
| 142 | NONYLAMINE | 4.88,a | m/z 569.95 (M + H) | C26H35Br2NO3 | B |
| 143 | 2,5-DICHLOROBENZYLAMINE | 4.49,a | m/z 601.72 (M + H) | C24H21Br2Cl2NO3 | B |
| 144 | 2-METHYLCYCLOHEXYLAMINE | 4.44,a | m/z 539.91 (M + H) | C24H29Br2NO3 | B |
| 145 | 3-METHYLCYCLOHEXYLAMINE | 4.51,a | m/z 539.90 (M + H) | C24H29Br2NO3 | B |
| 146 | 3-N-PROPOXYPROPYLAMINE | 4.30,a | m/z 543.90 (M + H) | C23H29Br2NO4 | B |
| 147 | 2,3-DIMETHYLBENZYLAMINE | 4.48,a | m/z 561.91 (M + H) | C26H27Br2NO3 | B |
| 148 | 3-CHLOROBENZYLAMINE | 4.40,a | m/z 567.79 (M + H) | C24H22Br2ClNO3 | B |
| 149 | 4-TERT-BUTYLCYCLOHEXYLAMINE | 4.80,a | m/z 581.97 (M + H) | C27H35Br2NO3 | B |
| 150 | (1S,2S)-(+)-THIOMICAMINE | 3.94,a | m/z 639.80 (M + H) | C27H29Br2NO5S | B |
| 151 | 2,4-DIMETHYLBENZYLAMINE | 4.49,a | m/z 561.89 (M + H) | C26H27Br2NO3 | B |
| 152 | 2-AMINOETHYL PHENYL SULFIDE | 4.44,a | m/z 579.83 (M + H) | C25H25Br2NO3S | B |
| 153 | PHENETHYLAMINE | 4.36.a | m/z 547.87 (M + H) | C25H25Br2NO3 | B |
| 154 | TYRAMINE | 4.04,a | m/z 563.86 (M + H) | C25H25Br2NO4 | B |
| 155 | L-TYROSINE METHYL ESTER | 4.01,a | m/z 621.97 (M + H) | C27H27Br2NO6 | B |
| 156 | BENZHYDRYLAMINE | 4.52,a | m/z 609.82 (M + H) | C30H27Br2NO3 | B |
| 157 | 4-METHOXYBENZYLAMINE | 4.25,a | m/z 563.85 (M + H) | C25H25Br2NO4 | B |
| 158 | 2,3-DICHLOROBENZYLAMINE | 4.52,a | m/z 601.71 (M + H) | C24H21Br2Cl2NO3 | B |
| 159 | GLYCINE N-BUTYL ESTER HYDROCHLORIDE | 4.03,b | m/z 557.85 (M + H) | C23H27Br2NO5 | B |
| 160 | D-(−)-ALPHA-PHENYLGLYCINE ETHYL ESTER HYDROCHLORIDE | 4.11,b | m/z 605.84 (M + H) | C27H27Br2NO5 | B |
| 161 | 4-CHLORO-2-FLUOROBENZYLAMINE HYDROCHLORIDE | 4.27,b | m/z 585.80 (M + H) | C24H2IBr2ClFNO3 | B |
| 162 | TRANS-2-PHENYLCYCLOPROPYLAMINE HYDROCHLORIDE | 4.22,b | m/z 559.86 (M + H) | C26H25Br2NO3 | B |
| 163 | ETHYL 4-AMINOBUTYRATE HYDROCHLORIDE | 3.87,b | m/z 557.85 (M + H) | C23H27Br2NO5 | B |
| 164 | DL-HOMOCYSTEINE THIOLACTONE HYDROCHLORIDE | 3.65,b | m/z 543.80 (M + H) | C21H21Br2NO4S | B |
| 165 | 4-NITROBENZYLAMINE HYDROCHLORIDE | 3.99,b | m/z 578.85 (M + H) | C24H22Br2N2O5 | B |
| 166 | NORPHENYLEPHRINE HYDROCHLORIDE | 3.60,b | m/z 579.84 (M + H) | C25H25Br2NO5 | B |
| 167 | GLYCINE ETHYL ESTER HYDROCHLORIDE | 3.71,b | m/z 529.87 (M + H) | C21H23Br2NO5 | B |
| 168 | DL-ALANINE ETHYL ESTER HYDROCHLORIDE | 3.83,b | m/z 543.86 (M + H) | C22H25Br2NO5 | B |
| 169 | SARCOSINE ETHYL ESTER HYDROCHLORIDE | 3.79,b | m/z 543.92 (M + H) | C22H25Br2NO5 | B |
| 170 | 4-NITRO-N-PROPYLBENZYL AMINE HYDROCHLORIDE | 4.29,b | m/z 620.89 (M + H) | C27H28Br2N2O5 | B |
| 171 | PIPERIDINE | 3.98,b | m/z 511.93 (M + H) | C22H25Br2NO3 | B |
| 172 | 3-METHYLPIPERIDINE | 4.14,b | m/z 525.91 (M + H) | C23H27Br2NO3 | B |
| 173 | 3-(HYDROXYMETHYL)-PIPERIDINE | 3.66,b | m/z 541.89 (M + H) | C23H27Br2NO4 | B |
| 174 | 1,2,3,4-TETRAHYDROISOQUINOLINE | 4.23,b | m/z 559.85 (M + H) | C26H25Br2NO3 | B |
| 175 | 2-ETHYLPIPERIDINE | 4.25,b | m/z 539.90 (M + H) | C24H29Br2NO3 | B |
| 176 | 3,4-DICHLORO-N-ETHYLBENZYLAMINE | 4.54,b | m/z 629.75 (M + H) | C26H25Br2Cl2NO3 | B |
| 177 | 2-METHYLPYRROLIDINE | 3.99,b | m/z 511.90 (M + H) | C22H25Br2NO3 | B |
| 178 | N-ETHYL-N-PROPYLAMINE | 4.11,b | m/z 513.89 (M + H) | C22H27Br2NO3 | B |
| 179 | 4-METHYLPIPERIDINE | 4.15,b | m/z 525.91 (M + H) | C23H27Br2NO3 | B |
| 180 | (S)-(+)-2-(METHOXYMETHYL) PYRROLIDINE | 3.99,b | m/z 541.90 (M + H) | C23H27Br2NO4 | B |
| 181 | N-BENZYLETHANOLAMINE | 4.01,b | m/z 577.86 (M + H) | C26H27Br2NO4 | B |
| 182 | DIBENZYLAMINE | 4.56,b | m/z 623.79 (M + H) | C31H29Br2NO3 | B |
| 183 | 4-BENZYL-4-HYDROXYPIPERIDINE | 4.12,b | m/z 617.88 (M + H) | C29H31Br2NO4 | B |
| 184 | (R)(−)-2-BENZYLAMINO-1-BUTANOL | 4.16,b | m/z 605.83 (M + H) | C28H31Br2NO4 | B |
| 185 | N-(N-ETHYLAMINOACETYL)-2,6-DIMETHYLANILINE | 4.00,b | m/z 632.69 (M + H) | C29H32Br2N2O4 | B |

-continued

| Example | —NR'R" | HPLC[1] | MS[2] | Formula | Method[3] |
|---|---|---|---|---|---|
| 186 | N-ETHYL-O-METHOXYBENZYLAMINE | 4.35,b | m/z 591.93 (M + H) | C27H29Br2NO4 | B |
| 187 | MAYBRIDGE NRB 01961 | 4.40,b | m/z 647.88 (M + H) | C30H33Br2NO5 | B |
| 188 | 2-((N-ETHYLAMINO)METHYL)-4-NITROPHENOL | 4.05,b | m/z 622.80 (M + H) | C26H26Br2N2O6 | B |
| 189 | MAYBRIDGE SEW 01484 | 4.48,b | m/z 671.89 (M + H) | C31H29Br2NO4S | B |
| 190 | 3-AZABICYCLO-[3.2.2]NONANE | 4.28,b | m/z 551.89 (M + H) | C25H29Br2NO3 | B |
| 191 | N-(2-METHOXY-ETHYL)ETHYLAMINE | 3.89,b | m/z 529.88 (M + H) | C22H27Br2NO4 | B |

EXAMPLES 192–203

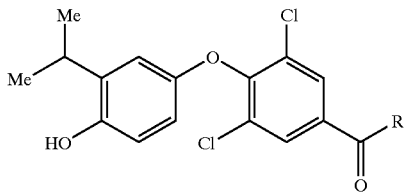

General Procedure 3,5-Dichloro-4-(4-hydroxy-3-isopropylphenoxy)benzoic acid was coupled with the appropriate amino acid, using the general procedure outlined for Examples 3–24. The residue was subjected to semi-preparative HPLC, using the same gradient elution as outlined for Examples 3–24. The amine part "R" and the stereochemistry of the aminoacids is indicated in the table below. Retention times, yields and the mass of the individual products are also given below.

| Example | R | Yield (%) | MS m/z (M + H)[1] | HPLC |
|---|---|---|---|---|
| 192 | | 64 | 407.3 | 7.3 |
| 193 | | 61 | 426.1 | 7.1 |
| 194 | | 59 | 435.2 | 6.6 |
| 195 | | 40 | 440.1 | 6.7 |
| 196 | | 88 | 452.3 | 6.6 |
| 197 | | 76 | 452.2 | 6.7 |
| 198 | | 71 | 453.2 | 6.5 |

-continued

| Example | R | Yield (%) | MS m/z (M + H)[1] | HPLC |
|---|---|---|---|---|
| 199 | (structure: -NH-CH2CH2-NH-phenyl) | 39 | 460.1 | 7.6 |
| 200 | (structure: -NH-(CH2)3-morpholine) | 55 | 467.9 | 6.7 |
| 201 | (structure: -NH-CH2CH2-NH-pyridyl-NO2) | 31 | 506.3 | 7.5 |
| 202 | (structure: -NH-piperidine-N-benzyl) | 72 | 514.4 | 7.0 |
| 203 | (structure: -NH-CH(CH2CH2SMe)-COOH) | 52 | 473.2 | 8.0 |

EXAMPLE 204

2-[3,5-Dibromo-4-(4-hydroxy-3-isopropylphenoxy) benzyl]-4-thiazole acetic acid (a) A reaction mixture of 3,5-dibromo-4-(4-methoxy-3-isopropylphenoxy)phenyl acetamide (150 mg) and Lawesson's reagent (100 mg) in dioxane (3 mL) was stirred at room temperature for 15 hours. The resulting suspension as filtered and poured onto ice-water and stirred. The water phase was extracted with EtOAc (3×7 mL) and the combined organic phases were washed with water. The organic phase was dried over $Na_2SO_4$, concentrated and gave 153 mg of crude 3,5-dibromo-4-(4-methoxy-3-isopropylphenoxy)phenyl thioamide. The crude product was used directly in the next step.

(b) To a suspension of 3,5-dibromo-4-(4-methoxy-3-isopropylphenoxy)phenyl thioamide (80 mg) in EtOH (2 mL), ethylchloroacetoacetonate (0.03 mL) was added. The mixture was stirred in a closed tube at 75° C. for 2 h. The reaction mixture was concentrated and EtOAc and water was added. The water phase was extracted with EtOAc (3×5 mL) and the combined organic phases were washed with $NaHCO_3$ (sat. solution). The organic phase was dried over $Na_2SO_4$, concentrated and purified by chromatography (silica gel, 15% EtOAc/p-ether). This gave 80 mg (86%) of ethyl-2-[3,5-dibromo-4-(4-hydroxy-3 isopropylphenoxy) benzyl]-4-thiazole acetate.

(c) $BF_3 \cdot Et_2$ (0.06 mL) was added slowly to a solution of the ethyl ester (60 mg) in $CH_2Cl_2$ (4 mL). The reaction mixture was stirred at room temperature for 2 days. Water was added. The water phase was extracted with EtOAc (3×5 mL) and the combined organic phases were washed with an aqueous solution of HCl (1N). The organic phase was dried over $Na_2SO_4$, concentrated and purified by semi-preparative HPLC. This gave 20 mg (37%) of the title compound.

EXAMPLE 205

2-[3,5-Dibromo-4-(4-hydroxy-3-isopropylphenoxy) benzyl]-4-methylthiazole (a) 3,5-dibromo-4-(4-methoxy-3-isopropylphenoxy)phenyl thioamide (70 mg) in EtOH (2 mL) was reacted with ethylchloroacetoacetonate (0.014 mL) using the method described in Example 204(b). The crude product was purified by chromatography (silica gel, 15% EtOAc/p-ether). This gave 60 mg (78%) of 2-[3,5-dibromo-4-(4-methoxy-3 isopropylphenoxy)benzyl]-4-methylthiazole.

(b) The above methoxy compound (50 mg) was demethylated with $BF_3 \cdot Et_2$ (0.06 mL), using the method described above. The crude mixture was purified by semi-preparative HPLC. This gave 20 mg (41%) of the title compound.

EXAMPLE 206

3,5-Dichloro-4-(4-hydroxy-3-isopropylphenoxy) phenylformylimino diacetic acid (a) To a solution of 3,5-dichloro-4-(4-methoxy-3-isopropylphenoxy)benzoic acid (60 mg, 0.169 mmol) in $CH_2Cl_2$ (10 mL) cooled with an ice-$H_2O$ bath was added diethyliminodiacetate (35.4 mg, 0.253 mmol), 1-[3-(dimethylamino) propyl]-3-ethylcarbodiimide hydrochloride (38.9 mg, 0.203 mmol) and 1-hydroxy-7-azabenzotriazole (27.6 mg, 0.203 mmol). The mixture was allowed to warm up to room temperature and left to stir overnight (ca. 18h). The mixture was taken up in EtOAc (50 mL) and H$_2$O (20 mL). The organic layer was separated and then it was washed successively with 1N HCl (2×25 mL), saturated NaHCO$_3$ aqueous solution (2×25 mL) and brine (2×25 mL). The organic extract was dried (Na$_2$SO$_4$), filtered and concentrated in vacuo. The crude product was purified by chromatography (25 g silica gel, 15% EtOAc in hexane) to give 31 mg of purified material (35% yield). Satisfactory proton and LC-MS were obtained.

(b) To a solution of above ethyl ester (25 mg, 0.047 mmol) in anhydrous CH$_2$Cl$_2$ (3 mL) cooled with an ice-H$_2$O bath was added boron tribromide (0.7 mL, 1.0 M in CH$_2$Cl$_2$, 0.7 mmol). After 2h, the mixture was poured into ice-H$_2$O (25 mL). After 15 min of stirring, the product was extracted with EtOAc (50 mL). The organic extract was washed with brine (2×25 mL), dried (MgSO$_4$), filtered and concentrated in vacuo. The crude product, a mixture of free acid and methyl ester, was dissolved in THF (2 mL) and 1N lithium hydroxide aqueous solution (1 mL) was added. After an hour, the mixture was acidified with 1N HCl and then extracted with EtOAc (25 mL). The EtOAc extract was washed with brine (2×15 mL), dried (Na$_2$SO$_4$), filtered and concentrated in vacuo to give 27.7 mg of crude product. The crude product was purified by prep HPLC to give 9.2 mg (38%) of of the title compound as a slightly yellow solid. Satisfactory proton and mass spectra were obtained.

EXAMPLE 207

N-[3,5-Dibromo-4-(4-hydroxy-3-isopropylphenoxy) benzoyl]-beta-alanine (a) 3,5-Dibromo-4-(4-hydroxy-3-isopropylphenoxy)benzoic acid (50 mg, 0.116 mmol), beta-alanine methyl ester hydrochloride (70 mg, 0.42 mmol), and hydroxy-benzotriazole (78 mg, 0.57 mmol) were dissolved in dichloromethane (0.6 mL), N,N-dimethylformamide (0.2 mL) and triethyl amine (0.12 mL, 0.58 mmol). The solution was cooled to 0° C. and 1-(3-dimethylaminopropyl)-3-ethylcarbodiimide hydrogen chloride (110 mg, 0.58 mmol) was added. The reaction was warmed to room temperature and stirred for 12 hours. The reaction was diluted with dichloromethane (100 mL) and washed with water (2×150 mL). The organic layer was washed once with brine (100 ml), dried over sodium sulfate and concentrated in vacuo. The methyl ester (50 mg, 90% yield) was purified by chromathography (silica gel, 7:3 hexane/ethyl acetate).

(b) The crude ester was dissolved in 1.0 mL of methanol and 0.4 mL of 1 N sodium hydroxide. The hydrolysis was complete in 2 hours. The methanol was removed and the aqueous layer was acidified with aqueous hydrochloric acid (1 N). The aqueous layer was extracted with ethyl acetate (3×100 mL). The combined organic layers were washed with brine (2×75 mL) and dried over sodium sulfate. The organic layer was concentrated in vacuo. The title compound (51 mg, 98%) was obtained without further purification. Satisfactory $^1$H-NMR, $^{13}$C-NMR and mass spectra was obtained for the title compound.

EXAMPLE 208

N-[3,5-Dichloro-4-(4-hydroxy-3-isopropylphenoxy) benzoyl]-beta-alanine (a) The ester was prepared by adding the reagents to the reaction in the manner described in Example 207. The starting acid (122 mg, 0.356 mmol), B-alanine methyl ester hydrochloride, and hydroxybenzotriazole (240 mg, 1.76 mmol) were dissolved in triethyl amine (0.6 mL, 2.5 mmol), dichloromethane 1.2 mL, and 0.8 mL of dimethylamide. The 1-(3-dimethylaminopropyl)-3-ethylcarbodiimide hydrogen chloride (110 mg, 0.58 mmol) was added in the manner as described above. The ester (75 mg, 50%) was isolated without further purification.

(b) The ester was dissolved in 3.0 mL of methanol and 1.6 mL of 1 N sodium hydroxide using the procedure described for title acid. The title acid (72 mg, 98% yield) was obtained from the reaction. The acid was further purified by preparative HPLC using a YMC ODS 20×100 mm column which yielded 53.6 mg (74% yield) of the purified acid.

EXAMPLE 209

L-N-[3,5-Dichloro-4-(4-hydroxy-3-isopropylphenoxy)benzoyl]serine 3,5-Dichloro-4-(4-hydroxy-3-isopropylphenoxy)benzoic acid (122 mg) was coupled with L-serin methyl ester hydrochloride using the method described in Example 207(a) and subsequently hydrolyzed using the method described in Example 207(b). The crude mixture was purified as above. Satisfactory $^1$H-NMR, $^{13}$C-NMR and mass spectra was obtained for the title compound.

EXAMPLE 210

D-N-[3,5-Dichloro-4-(4-hydroxy-3-isopropylphenoxy)benzoyl]serine 3,5-Dichloro-4-(4-hydroxy-3-isopropylphenoxy)benzoic acid (122 mg) was coupled with D-serin methyl ester hydrochloride using the method described in Example 207 (a) and subsequently hydrolyzed using the method described in Example 207(b). The crude mixture was purified as above. Satisfactory $^1$H-NMR, $^{13}$C-NMR and mass spectra was obtained for the title compound.

EXAMPLES 211–228

The compounds indicated in the table be low are all examples of further compounds, that can readily be prepared via the synthetic procedure described in Example 86.

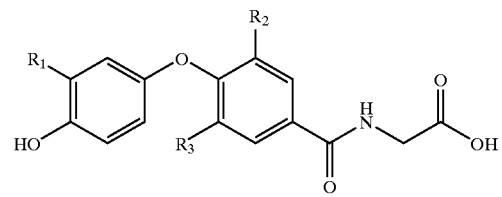

| Example | R₁ | R₂ | R₃ |
|---------|-----|-----|-----|
| 211 | Isopropyl | Me | Me |
| 212 | Isopropyl | Me | Br |
| 213 | Isopropyl | Me | Cl |
| 214 | Isopropyl | Me | I |
| 215 | Isopropyl | I | I |
| 216 | Isopropyl | I | Cl |
| 217 | Isopropyl | I | Br |
| 218 | Isopropyl | Br | Cl |
| 219 | I | Me | Me |
| 220 | I | Me | Br |
| 221 | I | Me | Cl |
| 222 | I | Me | I |
| 223 | I | I | I |
| 224 | I | Br | Cl |
| 225 | I | Br | Br |
| 226 | I | Cl | Cl |
| 227 | I | I | Br |
| 228 | I | I | Cl |

EXAMPLES 229–231

N-[3,5-Dichloro-4-(4-hydroxy-3-bromophenoxy)benzoyl]glycine

N-[3,5-Dichloro-4-(4-hydroxy-3-methylphenoxy)benzoyl]glycine

N-[3,5-Dichloro-4-(4-hydroxy-3-ethylphenoxy)benzoyl]glycine

These compounds were all prepared by a method analogous to that used in Example 86. Satisfactory ¹H-NMR, ¹³C-NMR and mass spectra were obtained for all three compounds.

What is claimed is:

1. A compound having the formula

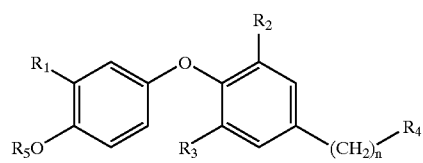

wherein
n is an integer from 0 to 4;
R₁ is $C_1$ to $C_6$ alkyl or $C_3$ cycloalkyl;
R₂ and R₃ are the same or different and are hydrogen, halogen, alkyl of 1 to 4 carbons, at least one of R₂ and R₃ being other than hydrogen;
R₄ is a carboxylic acid amide (CONR'R") in which R' and R" are the same or different and are independently selected from hydrogen, alkyl, aryl, and heteroaryl substituted or unsubstituted
R₅ is hydrogen or an acyl (such as acetyl or benzoyl) or other group capable of bioconversion to generate the free phenol structure (where in R₅=H);
including all stereoisomers thereof, prodrug esters thereof, and pharmaceutically acceptable salts thereof.

2. A compound as defined in claim 1 wherein R₄ is a carboxylic acid amide (CONR'R") in which the amine portion of the carboxylic amide can be derived from an achiral or a L or D alpha amino acid such as when the general structure —CONR'R" can be represented by

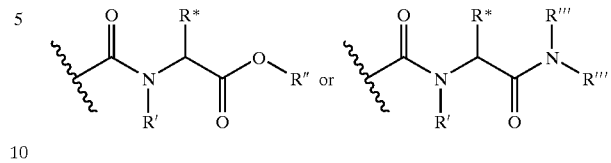

and R', R", R''', R'''', are the same or different and are independently selected from hydrogen, alkyl, aryl and heteroaryl, substituted or unsubstituted, and R* may be hydrogen, alkyl, aryl and heteroaryl, substituted or unsubstituted, and may also be any of the side chains found in the naturally occurring alpha-amino acids.

3. The compound as defined in claim 2 where R' and R* are connected to form a 4 to 8-membered ring.

4. The compound as defined in claim 2 where R' and R* comprise consecutive —(CH₂)— groups to form proline or homoproline.

5. The compound as defined in claim 1 where n is 0, 1, or 2.

6. The compound as defined in claim 1 wherein R₂ and R₃ are each independently halogen.

7. The compound as defined in claim 1 wherein R₂ and R₃ are each independently an alkyl group.

8. The compound as defined in claim 1 wherein one of R₂ and R₃ is halogen and the other is an alkyl group.

9. The compound as defined in claim 1 wherein one of R₂ and R₃ is halogen and the other in hydrogen.

10. The compound as defined in claim 1 wherein R₂ and R₃ is alkyl and the other is hydrogen.

11. The compound as defined in claim 1 wherein R₂ and R₃ are independently Cl, Br, methyl or ethyl.

12. The compound as defined in claim 1 wherein R₁ is isopropyl.

13. The compound as defined in claim 1 wherein R₅ is hydrogen.

14. The compound as defined in claim 1 which is in the table below,

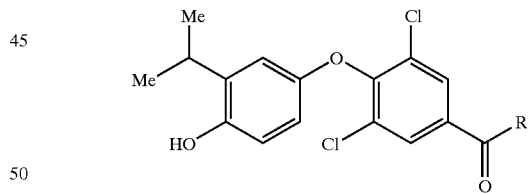

R =

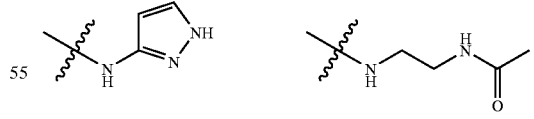

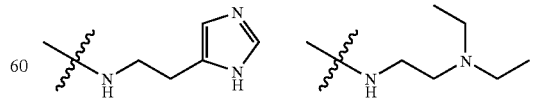

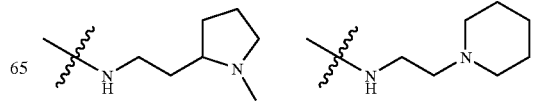

-continued

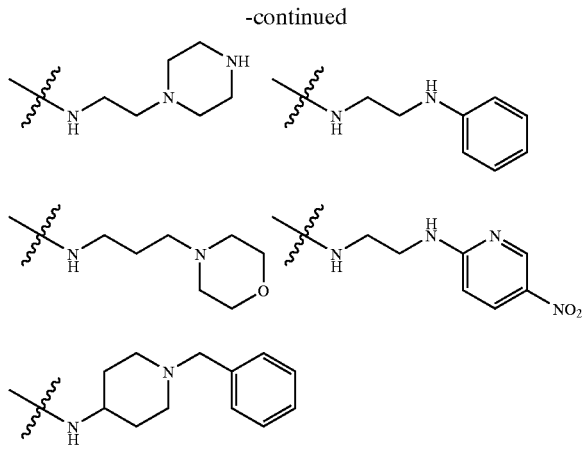

and the compounds indicated in the table below

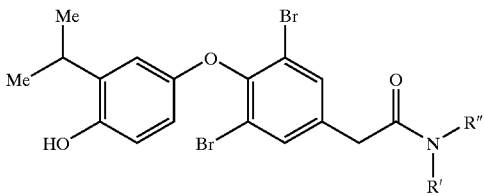

| —NR'R" | Formula |
|---|---|
| 3-(AMINOMETHYL)PYRIDINE | C23H22Br2N2O3 |
| 2-(2-AMINOETHYL)PYRIDINE | C24H24Br2N2O3 |
| 3-(2-AMINOMETHYL)PYRIDINE | C24H24Br2N2O3 |
| 2-(AMINOETHYL)PYRIDINE | C24H30Br2N2O3 |
| 4-(AMINOETHYL)PYRIDINE | C24H30Br2N2O3 |
| 1-(4-METHOXYPHENYL)PIPERAZINE DIHYDROCHLORIDE | C29H23Br2N2O3 |
| 1-(2-FLUOROPHENYL)PIPERAZINE | C34H32Br2N2O3 |
| 2-(2-AMINOETHYL)(PHENYLTHIO)BENZYL ALCOHOL | C31H29Br2N2O4S |
| 2-(1-CYCLOHEXENYL)ETHYLAMINE | C25H29Br2NO3 |
| 2-AMINOINDAN | C26H25Br2NO3 |
| 2-AMINOMETHYLBENZODIOXAN | C28H26Br2NO5 |
| 3-PHENYL-1-PROPYLAMINE | C26H27Br2NO3 |
| 2-(P-TOLYL)ETHYLAMINE | C26H27Br2NO3 |
| 1-(3-AMINOPROPYL)-2-PYRROLIDINONE | C24H28Br2N2O4 |
| BETA-ALANINE 4-METHOXY-BETA-NAPHTHYLAMIDE | C31H30Br2N2O5 |
| 2-CHLOROBENZYLAMINE | C24H22Br2ClNO3 |
| 2-AMINOMETHYL-3-CHLORODIPHENYLETHER | C30H26Br2ClNO4 |
| DL-ALPHA-AMINO-EPSILON-CAPROLACTAM | C23H26Br2N2O4 |
| L-PHENYLALANINOL | C26H27Br2NO4 |
| 4-(1,2,3-THIDIAZOL-4-YL)BENZYLAMINE | C26H28Br2N3O3S |
| 2-AMINOMETHYLTHIOPHENE | C22H21Br2NO3S |
| 1-(1-NAPHTHYL)ETHYLAMINE | C29H27Br2NO3 |
| 3-CHLORO-4-METHYL BENZYLAMINE | C25H24Br2ClNO3 |
| TETRAHYDROFURFURYLAMINE | C22H25Br2NO4 |
| 2,4-DICHLOROPHENETHYLAMINE | C25H23Br2Cl2NO3 |
| ETHYL 4-AMINO-1-PIPERIDINECARBOXYLATE | C25H30Br2N2O5 |
| 2,6-DIFLUOROBENZYLAMINE | C24H21Br2F2NO3 |
| 2-IODOBENZYLAMINE | C24H22Br2INO3 |
| 2-METHYLBENZYLAMINE | C25H26Br2NO3 |
| BENZYLAMINE | C24H23Br2NO3 |
| 3-METHYLBENZYLAMINE | C26H26Br2NO3 |
| 2-METHOXYPHENETHYLAMINE | C26H27Br2NO4 |
| 3-METHOXYPHENETHYLAMINE | C26H27Br2NO4 |
| 2-ETHOXYBENZYLAMINE | C26H27Br2NO4 |
| (R)-(−)-1-CYCLO-HEXYETHYLAMINE | C25H31Br2NO3 |
| 4-METHOXYPHENETHYLAMINE | C26H27Br2NO4 |
| 2-FLUOROBENZYLAMINE | C24H22Br2FNO3 |
| 2-CHLORO-6-METHYLBENZYLAMINE | C25H24Br2ClNO3 |
| 4-CHLOROBENZYLAMINE | C24H22Br2ClNO3 |
| BETA-METHYLPHENETHYLAMINE | C26H27Br2NO3 |
| 1,1-DI(P-ANISYL)METHYLAMINE | C32H31Br2NO5 |
| MAYBRIDGE BTB 12133 | C27H29Br2NO6 |
| DL-2-AMINO-1-PENTANOL | C22H27Br2NO4 |
| L-PHENYLALANINE P-NITROANILIDE | C32H29Br2N3O6 |
| ETHYL 3-AMINOBUTYRATE | C23H27Br2NO5 |
| (1S,2R)-(+)-2-AMINO-1,2-DIPHENYLETHANOL | C31H29Br2NO4 |
| 2-FLUOROPHENETHYLAMINE | C28H24Br2FNO3 |
| 2-ETHYLHEXYLAMINE | C26H33Br2NO3 |
| 3-FLUOROPHENETHYLAMINE | C26H24Br2FNO3 |
| (1S,2S)-(+)-2-AMINO-3-METHOXY-1-PHENYL-1-PROPANOL | C27H29Br2NO5 |
| NONYLAMINE | C26H35Br2NO3 |
| 2,5-DICHLOROBENZYLAMINE | C24H21Br2Cl2NO3 |
| 2-METHYLCYCLOHEXYLAMINE | C24H29Br2NO3 |
| 3-METHYLCYCLOHEXYLAMINE | C24H29Br2NO3 |
| 3-N-PROPOXYPROPYLAMINE | C23H29Br2NO4 |
| 2,3-DIMETHYLBENZYLAMINE | C26H27Br2NO3 |
| 3-CHLOROBENZYLAMINE | C24H22Br2ClNO3 |
| 4-TERT-BUTYLCYCLOHEXYLAMINE | C27H35Br2NO3 |
| (1S,2S)-(+)-THIOMICAMINE | C27H29Br2NO5S |
| 2,4-DIMETHYLBENZYLAMINE | C26H27Br2NO3 |
| 2-AMINOETHYL PHENYL SULFIDE | C25H25Br2NO3S |
| PHENETHYLAMINE | C25H26Br2NO3 |
| TYRAMINE | C25H25Br2NO4 |
| L-TYROSINE METHYL ESTER | C27H27Br2NO6 |
| BENZHYDRYLAMINE | C30H27Br2NO3 |
| 4-METHOXYBENZYLAMINE | C25H25Br2NO4 |
| 2,3-DICHLOROBENZYLAMINE | C24H21Br2Cl2NO3 |
| GLYCINE N-BUTYL ESTER HYDROCHLORIDE | C23H27Br2NO5 |
| D-(−)-ALPHA-PHENYLGLYCINE ETHYL ESTER HYDROCHLORIDE | C27H27Br2NO5 |
| 4-CHLORO-2-FLUOROBENZYLAMINE HYDROCHLORIDE | C24H21Br2ClFNO3 |
| TRANS-2-PHENYLCYDLOPROPYLAMINE HYDROCHLORIDE | C26H26Br2NO3 |
| ETHYL 4-AMINOBUTYRATE HYDROCHLORIDE | C23H27Br2NO5 |
| DL-HOMOCYSTEINE THIOLACTONE HYDROCHLORIDE | C21H21Br2NO4S |
| 4-NITROBENZYLAMINE HYDROCHLORIDE | C24H22Br2N2O5 |
| NORPHENYLEPHRINE HYDROCHLORIDE | C25H25Br2NO5 |
| GLYCINE ETHYL ESTER HYDROCHLORIDE | C21H23Br2NO5 |
| DL-ALANINE ETHYL ESTER HYDROCHLORIDE | C22H26Br2NO5 |
| SARCOSINE ETHYL ESTER HYDROCHLORIDE | C22H26Br2NO5 |
| 4-NITRO-N-PROPYLBENZYLAMINE HYDROCHLORIDE | C27H28Br2N2O5 |
| PIPERIDINE | C22H25Br2NO3 |
| 3-METHYLPIPERIDINE | C23H27Br2NO3 |
| 3-(HYDROXYMETHYL)-PIPERIDINE | C23H27Br2NO4 |
| 1,2,3,4-TETRAHYDROISOQUINOLINE | C26H26Br2NO3 |
| 2-ETHYLPIPERIDINE | C24H29Br2NO3 |
| 3,4-DICHLORO-N-ETHYLBENZYLAMINE | C26H25Br2Cl2NO3 |
| 2-METHYLPYRROLIDINE | C22H25Br2NO3 |
| N-ETHYL-N-PROPYLAMINE | C22H27Br2NO3 |
| 4-METHYLPIPERIDINE | C23H27Br2NO3 |
| (S)-(+)-2-(METHOXYMETHYL)PYRROLIDINE | C23H27Br2NO4 |
| N-BENZYLETHANOLAMINE | C26H27Br2NO4 |
| DIBENZYLAMINE | C31H29Br2NO3 |
| 4-BENZYL-4-HYDROXYPIPERIDINE | C29H31Br2NO4 |
| (R)(−)-2-BENZYLAMINO-1-BUTANOL | C28H31Br2NO4 |
| N-(N-ETHYLAMINOACETYL)-2,6-DIMETHYLANILINE | C29H32Br2N2O4 |
| N-ETHYL-O-METHOXYBENZYLAMINE | C27H29Br2NO4 |
| MAYBRIDGE NRB 01961 | C30H33Br2NO5 |
| 2-((N-ETHYLAMINO)METHYL)-4-NITROPHENOL | C26H25Br2N2O6 |
| MAYBRIDGE SEW 01484 | C31H29Br2NO4S |
| 3-AZABICYCLO-[3.2.2]NONANE | C25H29Br2NO3 |
| N-(2-METHOXY-ETHYL)ETHYLAMINE | C22H27Br2NO4 |

15. The compound as defined in claim 1 which is
D-N-[3,5-Dibromo-4-(4-hydroxy-3-isopropylphenoxy)benzoyl]valine,
D-N-[3,5-Dibromo-4-(4-hydroxy-3-isopropylphenoxy)benzoyl]leucine,
L-S-Benzyl, N-[3,5-dibromo-4-(4-hydroxy-3-isopropylphenoxy)benzoyl]cysteine,
D-N-[3,5-Dibromo-4-(4-hydroxy-3-isopropylphenoxy)benzoyl]tyrosine,
N-[3,5-dibromo-4-(4-hydroxy-3-isopropylphenoxy)benzoyl]arginine,
L-N-[3,5-Dibromo-4-(4-hydroxy-3-isopropylphenoxy)benzoyl]aminobutyric acid,
L-N-[3,5-Dibromo-4-(4-hydroxy-3-isopropylphenoxy)benzoyl]valine,
L-N-[3,5-Dibromo-4-(4-hydroxy-3-isopropylphenoxy)benzoyl]leucine,
L-N-[3,5-Dibromo-4-(4-hydroxy-3-isopropylphenoxy)benzoyl]proline,
L-N-[3,5-Dibromo-4-(4-hydroxy-3-isopropylphenoxy)benzoyl]cysteine,
N-[3,5-Dibromo-4-(4-hydroxy-3-isopropylphenoxy)benzoyl]glycine,
L-N-a-[3,5-Dibromo-4-(4-hydroxy-3-isopropylphenoxy)benzoyl]lysine,
D-N-a-[3,5-Dibromo-4-(4-hydroxy-3-isopropylphenoxy)benzoyl]lysine,
N-[3,5-Dibromo-4-(4-hydroxy-3-isopropylphenoxy)benzoyl]aminoisobutyric acid,
L-N-[3,5-Dibromo-4-(4-hydroxy-3-isopropylphenoxy)benzoyl]phenylglycine,
D-N-[3,5-Dibromo-4-(4-hydroxy-3-isopropylphenoxy)benzoyl]phenylglycine,
N-[3,5-Dibromo-4-(4-hydroxy-3-isopropylphenoxy)benzoyl]sarcosine,
DL-N-[3,5-Dibromo-4-(4-hydroxy-3-isopropylphenoxy)benzoyl]-a-methylphenylalanine,
L-N-[3,5-Dibromo-4-(4-hydroxy-3-isopropylphenoxy)benzoyl]isoleucine,
D-N-[3,5-Dibromo-4-(4-hydroxy-3-isopropylphenoxy)benzoyl]methionine,
L-N-[3,5-Dibromo-4-(4-hydroxy-3-isopropylphenoxy)benzoyl]methionine,
L-N-[3,5-Dibromo-4-(4-hydroxy-3-isopropylphenoxy)benzoyl]phenylalanine,
D-N-[3,5-Dibromo-4-(4-hydroxy-3-isopropylphenoxy)benzoyl]phenylalanine,
L-N-[3,5-Dibromo-4-(4-hydroxy-3-isopropylphenoxy)benzoyl]cyclohexylalanine,
L-N-e-(Benzyloxycarbonyl), N-a-[3,5-dibromo-4-(4-hydroxy-3-isopropylphenoxy)-benzoyl]lysine,
D-N-e-(Benzyloxycarbonyl), N-a-[3,5-dibromo-4-(4-hydroxy-3-isopropylphenoxy)-benzyl]lysine,
D-N-[3,5-Dibromo-4-(4-hydroxy-3-isopropylphenoxy)benzoyl]homoserine,
N-[3,5-Dichloro-4-(4-hydroxy-3-isopropylphenoxy)benzoyl]glycine,
N-[3,5-Dichloro-4-(4-hydroxy-4-isopropylphenoxy)benzoyl]sarcosine,
3,5-Dichloro-4-(4-hydroxy-3-isopropylphenoxy)phenylformylimino diacetic acid,
N-[3,5-Dibromo-4-(4-hydroxy-3-isopropylphenoxy)benzoyl]-beta-alanine,
D-N-[3,5-Dichloro-4-(4-hydroxy-3-isopropylphenoxy)benzoyl]methionine,
L-N-[3,5-Dichloro-4-(4-hydroxy-3-isopropylphenoxy)benzoyl]serine D-N-[3,5-Dichloro-4-(4-hydroxy-3-isopropylphenoxy)benzoyl]serine
N-[3,5-Dichloro-4-(4-hydroxy-3-bromophenoxy)benzoyl]glycine
N-[3,5-Dichloro-4-(4-hydroxy-3-methylphenoxy)benzoyl]glycine
N-[3,5-Dichloro-4-(4-hydroxy-3-ethylphenoxy)benzoyl]glycine.

16. The compound as defined in claim 1 which is
D-N-[3,5-Dibromo-4-(4-hydroxy-3-isopropylphenoxy)phenylacetyl]methionine,
L-N-[3,5-Dibromo-4-(4-hydroxy-3-isopropylphenoxy)phenylacetyl]methionine,
D-N-[3,5-Dibromo-4-(4-hydroxy-3-isopropylphenoxy)phenylacetyl]a-methylalanine,
D-N-[3,5-Dibromo-4-(4-hydroxy-3-isopropylphenoxy)phenylacetyl]aspargine,
L-Methyl-N-[3,5-dibromo-4-(4-hydroxy-3-isopropylphenoxy)phenylacetyl]alanine,
L-N-[3,5-dibromo-4-(4-hydroxy-3-isopropylphenoxy)phenylacetyl]alanine,
L-Dimethyl-N-[3,5-dibromo-4-(4-hydroxy-3-isopropylphenoxy)phenylacetyl]glutamate,
L-Dimethyl-N-[3,5-dibromo-4-(4-hydroxy-3-isopropylphenoxy)phenylacetyl]glutamate,
L-(O-tert-butyl)methyl-N-[3,5-dibromo-4-(4-hydroxy-3-isopropylphenoxy)phenylacetyl]glutamate,
L-N-[3,5-dibromo-4-(4-hydroxy-3-isopropylphenoxy)phenylacetyl]glutamic acid,
L-N-[3,5-Dichloro-4-(4-hydroxy-3-isopropylphenoxy)phenylacetyl]aspartic acid,
D-di-tert-butyl-N-[3,5-dibromo-4-(4-hydroxy-3-isopropylphenoxy)phenylacetyl]glutamate,
D-N-[3,5-Dibromo-4-(4-hydroxy-3-isopropylphenoxy)phenylacetyl]glutamic acid,
L-O-tert-Butyl-N-[3,5-dibromo-4-(4-hydroxy-3-isopropylphenoxy)phenylacetyl]glutamine,
L-N-[3,5-Dibromo-4-(4-hydroxy-3-isopropylphenoxy)-phenylacetyl]glutamine,
D-N-[3,5-Dibromo-4-(4-hydroxy-3-isopropylphenoxy)phenylacetyl]glutamine,
L-O-Benzyl-N-[3,5-dibromo-4-(4-hydroxy-3-isopropylphenoxy)phenylacetyl]aspartic acid,
L-O-tert-Butyl-N-[3,5-dibromo-4-(4-hydroxy-3-isopropylphenoxy)phenylacetyl]asparagine,
L-Methyl-N-[3,5-dibromo-4-(4-hydroxy-3-isopropylphenoxy)phenylacetyl]homoserine,
L-N-[3,5-Dibromo-4-(4-hydroxy-3-isopropylphenoxy)phenylacetyl]homoserine,
D-Methyl-N-[3,5-dibromo-4-(4-hydroxy-3-isopropylphenoxy)phenylacetyl]homoserine,
and the compounds showed in the table below,

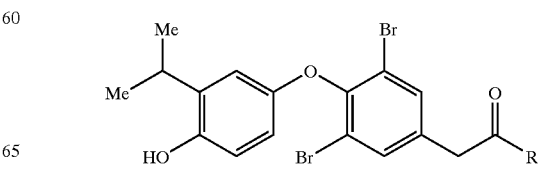

| R | Mol-Formel |
|---|---|
| L-Val | C22H26Br2NO6 |
| L-Val | C22H26Br2NO5 |
| L-Tyr | C26H26Br2NO6 |
| 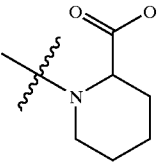 (L) | C23H27Br2NO5 |
| 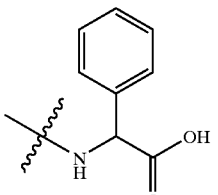 (L) | C27H27Br2NO5S |
| D-Leu | C23H27Br2NO6 |
| D-Tyr | C28H26Br2NO6 |
| D-Trp | C28H26Br2N2O6 |
| L-Arg | C23H28Br2N4O5 |
| L-Abu | C21H23Br2NO6 |
| 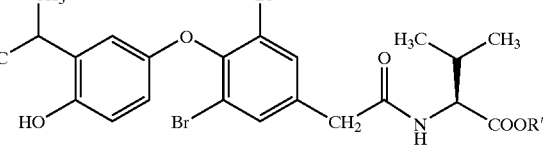 | C20H21Br2NO5 |
| 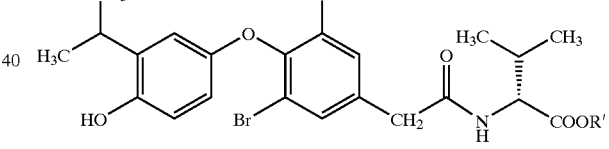 | C20H21Br2NO5 |
| L-Leu | C23H27Br2NO5 |
| 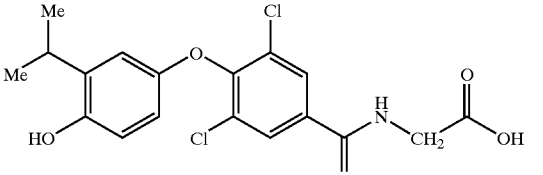 (L) | C25H23Br2NO5 |
| D-Pro | C22H23Br2NO5 |
| L-Ile | C23H27Br2NO5 |
| 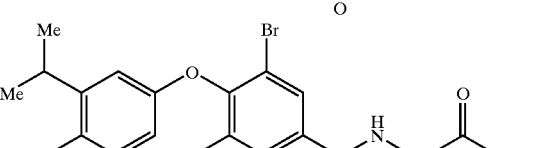 (D) | C23H26Br2NO5 |
| L-Phe | C26H26Br2NO5 |
| L-Lys | C23H28Br2N2O6 |

-continued

| R | Mol-Formel |
|---|---|
| (L) | C23H28Br2NO5 |
| L-Pro | C22H23Br2NO6 |
| (D) | C25H23Br2NO5 |

17. The compounds as defined in claim 1 having the structures or a pharmaceutically acceptable salt or ester(s) thereof.

18. The compounds as defined in claim 1 having the structures or a pharmaceutically acceptable salt or ester(s) thereof.

19. The compounds as defined in claim 1 having the structures

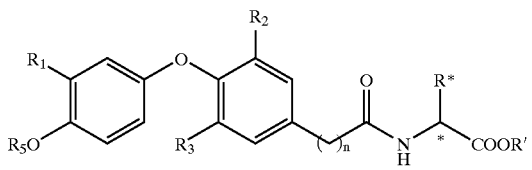

wherein $R_1$=isopropyl, methyl, ethyl; $R_2$ and $R_3$ may be independently selected from Br, Cl and Me; n=0 or 1; R* may be hydrogen, alkyl, cycloalkyl, aryl and heteroaryl; * denotes either D or L stereochemistry when R* is not hydrogen; $R_5$ is hydrogen; and R' is selected from hydrogen, lower alkyl, especially ethyl and methyl.

20. A pharmaceutical composition comprising an effective amount of a compound according to claim 1 or a pharmaceutically effective salt thereof, together with a pharmaceutically acceptable carrier.

21. A method to treat a skin disorder or disease selected from the group consisting of dermal atrophy, post surgical bruising caused by laser resurfacing, keloids, stria, cellulite, roughened skin, actinic skin damage, lichen planus, ichtyosis, acne, psoriasis, Dernier's diseases, eczema, atopic dermatitis, chloracne, pityriasis and skin scarring, said method comprising the step of administering to a patient a pharmaceutical composition comprising a therapeutically effective amount of a compound of claim 1.

* * * * *